United States Patent
Cury et al.

(10) Patent No.: US 9,109,041 B2
(45) Date of Patent: Aug. 18, 2015

(54) **ANALOG COMPOUNDS OF ANALGESIC PEPTIDES DERIVED FROM THE VENOM OF *CROTALUS DURISSUS TERRIFICUS* SNAKES, THEIR USES, COMPOSITIONS, METHODS OF PREPARATION AND PURIFICATION**

(75) Inventors: Yara Cury, Santana de Parnaiba (BR);
Gisele Picolo, São Paulo (BR);
Katsuhiro Konno, São Paulo (BR);
Renata Giorgi, São Paulo (BR);
Patricia Brigatte, São Paulo (BR);
Vanessa Gutierrez, São Paulo (BR);
Antônio Camargo, São Paulo (BR)

(73) Assignees: Yara Cury, Santana de Parnaiba (BR);
Fundacão De Amparo À Pesquisa Do Estado De São Paulo, São Paulo (BR);
Laboratório Biosintetica Ltda., São Paulo (BR)

( * ) Notice: Subject to any disclaimer, the term of this patent is extended or adjusted under 35 U.S.C. 154(b) by 2020 days.

(21) Appl. No.: 11/579,615

(22) PCT Filed: May 6, 2005

(86) PCT No.: PCT/BR2005/000073
§ 371 (c)(1),
(2), (4) Date: Feb. 9, 2009

(87) PCT Pub. No.: WO2005/107357
PCT Pub. Date: Nov. 17, 2005

(65) Prior Publication Data
US 2009/0203618 A1 Aug. 13, 2009

(30) Foreign Application Priority Data
May 6, 2004 (BR) .................................... 0401702
May 2, 2005 (BR) .................................... 0502399

(51) Int. Cl.
*C07K 14/46* (2006.01)
*C07K 7/08* (2006.01)
*A61K 38/00* (2006.01)

(52) U.S. Cl.
CPC . *C07K 14/46* (2013.01); *C07K 7/08* (2013.01); *A61K 38/00* (2013.01); *G01N 2800/2842* (2013.01)

(58) Field of Classification Search
None
See application file for complete search history.

(56) References Cited

U.S. PATENT DOCUMENTS

| 4,748,155 A | 5/1988 | Sisto et al. |
| 5,164,196 A * | 11/1992 | Plata et al. .................... 424/542 |
| 5,232,911 A * | 8/1993 | Vidal ........................... 514/19.3 |
| 5,439,884 A | 8/1995 | Spindel et al. |
| 5,866,346 A * | 2/1999 | Yu ................................ 435/7.21 |
| 2009/0203618 A1 * | 8/2009 | Cury et al. ....................... 514/14 |

FOREIGN PATENT DOCUMENTS

| EP | 0246861 | 11/1987 |
| WO | WO 91/01740 | 2/1991 |
| WO | WO 99/36078 | 7/1999 |
| WO | 2005/107357 | 11/2005 |

OTHER PUBLICATIONS

Faure et al. Multiplicity of acidic subunit isoforms of crotoxin, the phospholipase A2 neurotoxin from *Crotalus durissus terrificus* venom, results from posttranslational modifications. Biochemistry (1991), 30(32), 8074-83.*

Aird et al. Rattlesnake presynaptic neurotoxins: primary structure and evolutionary origin of the acidic subunit. Biochemistry (1985), 24(25), 7054-8 (Avail. online PubMed).*

Aird et al. Rattlesnake presynaptic neurotoxins: primary structure and evolutionary origin of the acidic subunit. Biochemistry (1985), 24(25), 7054-8.*

Faure et al. Multiplicity of acidic subunit isoforms of crotoxin, the phospholipase A2 neurotoxin from *Crotalus durissus terrificus* venom, results from posttranslational modifications Biochemistry (1991), 30(32), 8074-83.*

Aird et al., "Rattlesnake Presynaptic Neurotoxins: Primary Structure and Evolutionary Origin of the Acidic Subunit," *Biochemistry*, vol. 24, pp. 7054-7058, 1985.

European Search Report; Application Number: EP 05738454; search date: Apr. 16, 2008, pp. 1-3.

Faure et al., "Multiplicity of Acidic Subunit Isoforms of Crotoxin, the Phospholipase A2 Neurotoxin from *Crotalus durissus terrificus* Venom, Results from Posttranslational Modifications," *Biochemistry*, vol. 30, pp. 8074-8083, 1991.

Giorgi et al., "Analgesic Effect Evoked by Low Molecular Weight Substances Extracted from *Crotalus durissus terrificus* Venom," *Toxicon*, vol. 31, No. 10, pp. 1257-1265, 1993.

International Search Report; International Application No. PCT/BR05/00073; mailing date; Apr. 3, 2007; pp. 1-3.

Written Opinion; Application No. PCT/BR05/00073; mailing date Apr. 3, 2007, Applicant: Laboratorio Biosintetica LTDA; pp. 1-5.

Translation of Office Action issued in CN200880023231.7 on Jan. 30, 2012 (8 pages).

* cited by examiner

*Primary Examiner* — Maury Audet
(74) *Attorney, Agent, or Firm* — Fish & Richardson P.C.

(57) ABSTRACT

The present invention refers to analog compounds of peptides having the amino acid sequences SEQ ID NO: 1, SEQ ID NO: 2, SEQ ID NO: 3 or SEQ ID NO: 4, including analgesic peptides derived from snakes of species such as *Crotalus durissus terrificus*; their uses in the treatment, diagnosis and prevention of painful conditions or mediated by opioid receptors, their pharmaceutical compositions and their methods of preparation and purification, including their uses in the identification of analgesic compounds.

4 Claims, No Drawings

ANALOG COMPOUNDS OF ANALGESIC PEPTIDES DERIVED FROM THE VENOM OF *CROTALUS DURISSUS TERRIFICUS* SNAKES, THEIR USES, COMPOSITIONS, METHODS OF PREPARATION AND PURIFICATION

PRIORITY INFORMATION

This application is the U.S. national phase of PCT patent application PCT/BR2005/000073 filed on May 6, 2005 (published as WO 2005/107357 on Nov. 17, 2005), which claims benefit of Brazilian application no. PI0502399-8 (provisional no. 02005002) filed on May 2, 2005 and Brazilian application no. PI0401702-1 filed on May 6, 2004, the disclosures of which are incorporated by reference herein in their entireties.

FIELD OF INVENTION

The present invention refers to compounds that induce analgesia or act on opioid receptors in mammals. More specifically, this invention refers to analog compounds of peptides with analgesic effect derived from *Crotalus durissus terrificus* snake venom, their uses, pharmaceutical compositions and methods of preparation and purification.

BACKGROUND OF THE INVENTION

According to data from the Sociedade Brasileira para o Estudo da Dor [Brazilian Society for the Study of Pain] (SBED, 2004 http://www.dor.org.br/dor_impactos.asp), pain affects at least 30% of individuals at some moment of their lives and, from 10% to 40% of these individuals, pain lasts for more than one day. Pain is the main cause of suffering, work incapacity and it provokes serious psychosocial and economical consequences. Approximately 40% of these individuals miss many days of work. There are no official statistics about the impact of pain conditions in Brazilian population, however its occurrence has increased substantially in the last years. In addition, the incidence of chronic pain in the world oscillates from 7% and 40% of the population. As a consequence, from 50% to 60% of those individuals that suffer from chronic pain become partially or totally, temporarily or permanently incapacitated, significantly compromising life quality.

The therapeutic use of snake venoms observed in humans dates back to the beginning of the $20^{th}$ century (Brasil, V. Biol. Med. São Paulo, 1: 7-21, 1934, Brazil, V. An. Paul. Med. Cir., 60: 398-408, 1950; Klobusitzky D. Anais do Instituto Pinheiros, 1:3-23, 1938) and literature presents important reviews of the use of these venoms as therapeutic agents. These reviews show, for example, the use of the venom of *Crotalus adamanteus* for the treatment of epilepsy and the use of the venom from *Agkistrodon piscivorus*, *Vipera ruselli* and *Notechis scutatus* as haemostatic agents (Klobusitzky, D. Anais do Instituto Pinheiros, 1:3-23, 1938).

Reports about the analgesic property of snake venoms observed in humans date back to the beginning of the 30's decade (Monaelesser & Taguet, 1933, apud on Brazil, V. An. Paul. Med. Cir., 60: 398-408, 1950). Concerning the analgesic effect of the venom of the South American rattlesnake (*Crotalus durissus terrificus*), hereinafter referred to as "CdtV", the first studies were performed by Dr. Vital Brazil. In these studies, Dr. Vital Brazil prepared highly diluted crotalid venom solutions, denominated crotalid solute. The crotalid solution was distributed to several physicians in Brazil and abroad and it was used for the treatment of different pain conditions and disorders, mainly of neoplasic origin. The results of this study demonstrated that the rattlesnake's venom is highly effective in the treatment of different pain syndromes (Brazil, V. Biol. Med. São Paulo, 1: 7-21, 1934, Brazil, V. An. Paul. Med. Cir., 60: 398-408, 1950).

Concerning the use of snake venom-derived products for the treatment of painful conditions, the development of a product called anavenom, produced at Institute Butantan, by the mixture of these venoms with formaldehyde, is worth highlighting. These products were indicated for the treatment of different painful conditions, particularly in cases where usual analgesics had no effect. This product demonstrated potent analgesic effect, since this product could substitute the treatment with morphine. The anavenom also demonstrated long lasting analgesic effect, as patients were usually treated with anavenom with 1 to 3 days intervals between doses.

Despite the results observed by Dr. Vital Brazil, showing the analgesic effect of *Crotalus durissus terrificus* snake venom, the active substance, present in the crude venom, responsible for the analgesic effect, was not known.

Studies of the mechanisms of the analgesic action of this venom, using experimental models of pain evaluation, began in 1990.

These studies showed that CdtV, administered in mice, induces a long lasting antinociceptive effect, when evaluated in the hot plate test, suggesting that this venom is capable of causing analgesia through an action in the Central Nervous System (Giorgi R. et al., Toxicon, 31: 1257-65, 1993; Picolo G. et al. Toxicon 36:223-227, 1998). Pharmacological studies showed the involvement of kappa opioid receptors (Giorgi R. et al., Toxicon, 31: 1257-65, 1993; Brigatte P. et al. Toxicon 39:1399-1410, 2001), in antinociception observed in the hot plate test. Long treatments using the venom induced tolerance to the antinociceptive effect in the hot plate test, but not physical dependence. Tolerance is mediated by pharmacodynamic mechanisms. Crossed tolerance with morphine was not observed (Brigatte P. et al. Toxicon 39:1399-1410, 2001). On the other hand, due to the long lasting antinociceptive effect of the venom (5 days after the administration of a single dose), there is no development of the tolerance phenomenon if the venom is administered every 5 days, for up to 65 days after the beginning of the treatment (Brigatte P. et al. Toxicon 39:1399-1410, 2001).

In addition to the effect observed in the hot plate test, analgesic action was demonstrated for the crude venom in two experimental models of inflammatory pain: the model of the abdominal contortions induced by acetic acid (Giorgi R. et al., Toxicon, 31: 1257-65, 1993) and in hyperalgesia induced by carrageenin (Picolo G. et al., Eur J Pharmacol 391:55-62, 2000). In the carrageenin model, the analgesic effect of the venom is also a long lasting effect, persisting up to 5 days after the administration of one single dose of the venom. This effect involves the participation of peripheral delta opioid receptors (Picolo G. et al., Eur J Pharmacol 391:55-62, 2000).

On the other hand, in the model of hyperalgesia induced by prostaglandin, the antinociceptive action of the crotalid venom is mediated by kappa and delta opioid receptors (Picolo G. et al. Eur J Pharmacol 469:57-64, 2003). In both models of hyperalgesia (carrageenin and prostaglandin), the antinociception induced by the CdtV also involves the stimulation of the L-arginine/Nitric Oxide (NO)/cGMP pathway, of the cGMP-dependent protein kinase and activation of ATP-sensitive potassium channels (Picolo G. et al. Eur J Pharmacol 469:57-64, 2003, Picolo and Cury, Life Science 75:559-73, 2004).

It is important to emphasize that the venom is also able to induce antinociception in models of persistent pain, as in the model of neuropathic pain induced by chronic constriction of the sciatic nerve of rats (Gutierrez, V. P., Chacur, M., Sampaio, S. C., Picolo, G., Cury, Y. Memórias do Instituto Butantan vol. 60, p. 50, 2003) and in the model of cancer pain induced by the intraplantar injection of Walker 256 carcinoma cells in rats (Brigatte, P., Sampaio S. C., Gutierrez, V., Curi, R. Rangel-Santos, A. C., Guerra, J. L., Cury Y., XXXVI Congresso Brasileiro de Farmacologia e Terapêutica Experimental, Programa e Resumos, p. 195, 2004). The venom effect in the neuropathic pain model is also long, as it was detected for up to 3 days after the administration of a single dose of the venom. As observed in the models of hyperalgesia induced by carrageenin or prostaglandin, kappa and delta opioid receptors, the L-arginine/NO/cGMP pathway and opening of ATP-sensitive potassium channels are responsible for the effect of the venom in this model (Gutierrez, V. P., Chacur, M., Sampaio, S. C., Picolo, G., Cury, Y. Memórias do Instituto Butantan, vol. 60, p. 50, 2003).

Snake venoms are constituted by a complex mixture of proteins and biologically active peptides. Several active substances with different therapeutic indications were already isolated from these venoms. As examples, we have the patent U.S. Pat. No. 5,182,260 (Maraganore, J. H., 1993), where a polypeptide inhibitor of platelet activation was isolated from the North American *Water Moccasin* snake venom, or the patent U.S. Pat. No. 5,763,403 (Lyan, E. C. Y., 1998), where a lupus anticoagulant protein was obtained from the venom of *Agkistrodon halys brevicaudus* snakes, or the patent U.S. Pat. No. 6,489,451 (Li, B. X., 2002), where an antithrombotic enzyme was purified from the venom of *Agkistrodon acutus* snakes. In relation to products used in the treatment of pain, the American patent U.S. Pat. No. 6,555,109 (Shulov, A., 2003) describes a non-toxic fraction, isolated from the venom of *Vipera xanthina palestinae* snakes, and its derived products used to control diverse types of pain, including chronic pain. Furthermore, the American patent U.S. Pat. No. 6,613,745 (Gopalakrishnakone, P., 2003) presents peptides with sequences of amino acids derived or based on the amino acid sequence of an analgesic factor present in the venom of the King Cobra (*Ophiophagus hannah*).

The analgesic activity of crotamine, a toxin present in the venom of *Crotalus durissus terrificus* snakes, is also found in the literature. Studies demonstrated that there is an analgesic dose-response relationship, when purified crotamine is injected by s.c. or i.p. routes in mice. The analgesic effect was inhibited by naloxone, suggesting the involvement of opioid receptors (Mancin C. A. et al., Toxin 36:12, 1927-1937, 1998).

Opium and its derived products are potent analgesics, which also have other pharmacological effects. The endogenous and exogenous opioids are among the most used analgesics for pain control, particularly chronic or intractable pain, for example, cancer pain, neuropathic pain and chronic inflammatory pain. These drugs, by acting on specific receptors, induce analgesia in human beings and in animals, modifying the pathophysiological reponse to noxious chemical, mechanical or thermal stimuli (Yaksh, T. L. Acta Anaesth. Scand. 41:94-111, 1997).

At least three distinct families of endogenous opioid peptides were identified: the enkephalins, the endorphins and the dynorphins. Each family is derived from a distinct polypeptide precursor and has a characteristic anatomical distribution. These precursors, denominated proenkephalin, proopiomelanocortin and prodynorphin, have the Tyr-Gly-Gly-Phe-Met/Leu amino acid sequence (where Tyr, Gly, Phe, Met and Leu correspond to the tyrosine, glycine, phenylalanine, methionine and leucine amino acids, respectively), located in the N-terminal portion of the opioid peptides (Przewlocki R. and Przewlocka B. Eur. J. Pharmacol. 429:79-91, 2001, Reisine T. and Pasternak, G. In: The Pharmacolcogical Basis of Therapeutics, Hardman J. G. e Limbird L. E. eds, $9^{th}$ ed, New York, McGraw-Hill, pp. 521-555, 1996).

The opioids, by acting on afferent nerve endings, inhibit adenylyl cyclase, decreasing the production of cAMP (Schultz, J. E. J. and Gross, G. J. Pharmacol. Ther., 89:123-137, 2001) and inhibiting the opening of calcium channels, with consequent blocking of the release of neurotransmitters (Junien, J. L. and Wettstein, J. G. Life Science, 51:2009-18, 1992; Zaki, P. A. et al. Annu. Rev. Pharmacol. Toxicol., 36:379-401, 1996; Yaksh, T. L. Acta Anaesth. Scand. 41:94-111, 1997).

In addition, opioids activate the L-arginine-nitric oxide-GMPc pathway, inducing potassium channel opening, with consequent hyperpolarization of the cellular membrane (Ferreira, S. H. et al. Eur. J. Pharmacol., 1217: 225-7, 1991; Ferreira, S. H. et al. Br. J. Pharmacol., 114: 303-8, 1995; Nozaki-Taguchi, N. and Yamamoto, T. Anesth. Anal., 87: 388-93, 1998; Amarante, L. H and Duarte, I. D. Eur J Pharmacol., 454:19-23, 2002). The antinociceptive effect of opioid agonists on $K^+$ channels involves both the ATP sensitive and the voltage-dependent $K^+$ channels (Welch, S. and Dunlow, L. D. J. Pharmacol. Exp. Ther., 267:390-399, 1993; Rodrigues, A. R A. and Duarte I. D. G. Br. J. Pharmacol, 129:110-114, 2000; Schultz, J. E. J. and Gross, G. J. Pharmacol. Ther., 89:123-137, 2001).

Additionally, several studies have shown that opioid analgesics, including κ opioid agonists affect the mitogen-activated protein kinase (MAPK) (Li, J. G., et al, J. Biol. Chem., 274:12087-12094, 1999; Eitan, S. et al, J. Neuroscience, 23:8360-8369, 2003; Lesscher, H. M. B. et al, Neuroscience, 116:139-144, 2003).

Besides the existence of multiple peptides that present opioid activity, the existence of multiple opioid receptors was pharmacologically characterized. Thus, it is considered that opioid analgesics induce their effects by interaction with specific receptors, constituted of at least 3 main classes: μ (mu), κ (kappa) and δ (delta) (Yaksh, T. L. Eur. J. Anaesthesiol. 1:201-243, 1984), distributed in the Central Nervous System and in peripheral tissues, with distinct pharmacological activities, anatomical distribution and function (Junien, J. L. and Wettstein, J. G. Life Science, 51:2009-2018, 1992; Yaksh, T. L. Acta Anaesth. Scand. 41:94-111, 1997).

The central and peripheral actions of opioids are important components of their therapeutic use. The mu receptors are responsible for most of the analgesic effects of the opioids and for some of their adverse effects, such as respiratory and cardiovascular depression, euphoria, dependence, sedation and alteration of several neuroendocrine functions [Brownstein, M. J. Proc. Natl. Acad. Sci. (USA), 90:5391-5393, 1993].

These secondary effects occur mainly as a consequence of the action of these agonists in the Central Nervous System. This is the main reason for the underuse of opioid analgesics in pain control. Delta opioid receptors are, probably, more important in the periphery, although they also cause central analgesia. In addition to analgesia, these receptors modulate gastrointestinal motility and several hormonal functions. On the other hand, kappa opioid receptors induce analgesia without causing the adverse effects characteristic of μ receptors, such as constipation, itch, respiratory depression, physical dependence and/or addiction. However, the kappa receptors maintain some centrally mediated effects, such as sedation and dysphoria, but not physical dependence (Vanvoigtlander et al., J. Pharmacol. Exp. Ther., 224: 7-12, 1983; Wood, P. L.

and Iyengar, S. In: The opioid receptors. Pasternak, G. W. ed. Humana press, Clifton, N.Y., 1988). These receptors are responsible for drinking balance, food intake, intestinal motility, temperature control and several endocrine functions (Leander, J. Pharmacol. Exp. Ther., 227: 35-41, 1983; Leander et al., J. Pharmacol. Exp. Ther. 234, 463-469, 1985; Morley et al., Peptides 4, 797-800, 1983; Manzanares et al., Neuroendocrinology 52, 200-205, 1990; Iyengar et al., J. Pharmacol. Exp. Ther., 238, 429-436, 1986).

Morphine and codeine, the most clinically used opioid analgesics, act as agonists of mu opioid receptors. These opioids cause well-known undesirable adverse effects, for example, the development of physical dependence. Kappa or delta receptor agonists act as analgesics by acting on kappa and delta opioid receptors, respectively. The advantage of these agonists over the classic agonists of mu receptors, e.g morphine, results from their ability to cause analgesia without inducing the undesirable secondary behavioral effects described for morphine. It is known that the structural relationship between opioid receptor and its ligand is responsible for selectivity and specificity for the receptor. Nevertheless, several studies indicate that specific interactions of the opioid receptors with several membrane compartments can contribute to the ability of these opioids to interact selectively with specific receptors (Janecka A. et al. Mini Rev Med Chem. 2:565-572, 2002; Naito A. and Nishimura K. Curr Top Med Chem. 4:135-145, 2004; Singh VK et al. Neuroimmunomodulation. 4:285-297, 1997). This invention refers to novel peptides which are not homologous to the enkephalins, endorphins or dynorphins, and also to the synthetic peptides with preferential activity on kappa opioid receptors.

It is known in the literature that the occurrence of adverse effects using opioids for therapeutic purposes, decreases when opioid specificity and selectivity increases for a specific type or subtype of receptors. Those agonists that have affinity for kappa and/or delta opioid receptors, have demonstrated potent analgesic activity, without presenting serious adverse effects, such as physical dependence, respiratory depression and inhibition of smooth musculature movement, effects that are observed for morphine and agonist derivatives of mu receptors (Nagase, H.; Kawai, K.; Kawamura, K.; Hayakawa, J.; Endoh, T.; patent U.S. Pat. No. 6,323,212, 2001). Adverse effects such as physical dependence and respiratory depression induced by opioids are associated with the action of these drugs on Central Nervous System. The conventional opioids like morphine, naloxone, levorphanol, enkephalins, endorphins and dynorphins and analogs are generally hydrophobic molecules. Therefore, these opioids are able to permeate membranes such as blood-brain barrier, easily accumulating in adipose tissues and organs. This permeability has been also associated with adverse effects in the Central Nervous System, such as euphoria and addiction. Furthermore, these peptides must be administered in high doses, which cause toxic reactions associated with the long exposure to opioids (patent U.S. Pat. No. 5,602,100; Brown, W. L., 1997). Some patents were found in the state of art suggesting the combined use of various antagonists and agonists, formulated or not, as antinociceptive and anti-inflammatory agents. These studies suggest the use of pharmaceutical compositions with concomitant action in different nociceptive pathways and/or inflammatory mechanisms, interfering in the origin of both processes (nociceptive and inflammatory), for example, in surgical processes as oral and/or dental procedures. These agents can be: a 5HT-2 receptor antagonist, a 5HT-3 receptor antagonist, histamine antagonist, serotonin agonist, cyclooxygenase inhibitor, neurokinin 1 receptor antagonist, neurokinin 2 receptor antagonist, purinoreceptors antagonist, calcium channel antagonist, bradykinin B1 receptor antagonist, bradykinin B2 receptor antagonist and a mu opioid receptor agonist. Furthermore, the association of drugs for the treatment of cartilage destruction is also described in these patents and published applications (patent U.S. Pat. No. 6,420,432; Demopulos, G., 2002; US2003096807 A1; Demopulos, G., 2003).

Many works about molecular pharmacology and genetic manipulation of opioid peptides, opioid receptors and opioid receptors agonists and antagonists were found in the state of art. These studies covered the biochemical and molecular effects of opioids, the endogenous opioids neurochemical localization and their behavior-related receptors. Furthermore, the relation of these opioids with analgesia and pain, stress, tolerance and dependence, learning and memory, alcohol and drug abuse, sexual and hormonal activity, pregnancy and endocrine development, general brain activity and locomotion, neurological disorders, gastrointestinal, renal and hepatic functions, and cardiovascular responses were also investigated (Bodnar, R and Hadjimarkou, Peptides, 24, 1241-1302, 2003).

In patent U.S. Pat. No. 5,866,346 (Yu. L., 1999), Lei Yu describes the method of use of dynorphins as ligands for the XOR1 receptor. Therefore, compounds that are preferential kappa opioid receptors agonists, could be ligands for XOR1 receptors.

Although the use of snake venoms and of peptides that act on opioid receptors have been described in the Literature, the nature of the active analgesic substance present in *Crotalus durissus terrificus* snake venom, or its effectiveness, when administered in the purified form, including oral administration routes, has not been determined yet. Such data also did not explain the effectiveness of compounds analogs to such active substance, nor their specific action on opioid receptors.

DESCRIPTION OF THE INVENTION

This invention is based on the discovery and characterization of the active analgesic substance present in the venom of *Crotalus durissus terrificus* snake. It also confirms the analgesic effect of such substance when administered in its purified form, including oral administration route. This invention is also based on the evidence of the analgesic effectiveness of analog compounds of the active substance present in *Crotalus durissus terrificus* snake venom, as well as on the evidence of the action of such compounds on opioid receptors.

As the first main independent aspect, this invention refers to novel analog compounds to the analgesic substance present in the venom of *Crotalus durissus terrificus* snake, which have pharmacological properties that mimic compounds with the structure:

```
                                              (SEQ ID NO: 1)
Xaa-R1-Ser-R2-R3-R4-Cys-Glx-Gly-R5-Ser-R6-Pro-Cys
``` wherein:

Xaa is always pyroglutamate,

R1=Phe or Trp or Tyr or Leu or Thr,

R2=Pro or Arg,

R3=Glx or Asx or Gly,

R4=Asn or Gln or Leu,

R5=Glx or Asx,

R6=Glx or Lys, their salts, solvates or analog compounds, except when the compound is a tetradecapeptide wherein R1=Phe, R2=Pro, R3=Glu, R4=Asn, R5=Glu and R6=Gln, the cysteine residues in positions 7 and 14 are linked by an intramolecular disulfide bridge (SEQ ID NO: 2).

More specifically, this invention refers to compounds according to SEQ ID NO: 1, characterized by the cysteine residues in positions 7 and 14 that are linked by an intramolecular disulfide bridge (SEQ ID NO: 4); in particular analog compounds to tetradecapeptide with the amino acid sequence Xaa-Phe-Ser-Pro-Glu-Asn-Cys-Gln-Gly-Glu-Ser-Gln-Pro-Cys, wherein Xaa is pyroglutamate and the cysteine residues in positions 7 and 14 are linked by an intramolecular disulfide bridge (SEQ ID NO: 2); as for example tetradecapeptides that present the sequence of peptides SEQ ID NO: 1 or SEQ ID NO 4.

According to this invention, the concept "analog compounds" is applied to compounds that have chemical structure with portions that present, even though partially, pharmacological properties of peptides of the sequences SEQ ID NO: 1, SEQ ID NO: 2, SEQ ID NO: 3 and SEQ ID NO: 4 in relation to their analgesic action or of their direct or indirect interaction, agonist or antagonist, with opioid receptors.

As a complementary aspect, the present invention also includes compounds that mimic pharmacological properties of peptides that contain SEQ ID NO: 1, SEQ ID NO: 2, SEQ ID NO: 3 and SEQ ID NO 4 characterized by adding, deleting or altering peptide-mimetic properties, for modulation of their pharmacokinetic and pharmacodynamic properties, including the substitution of one or more L-amino acids for D-amino acids or non-conventional amino acids or even by presenting of the proline residue in position 4 or γ-carboxylation of the glutamate residues in positions 5 or 10. Examples of D-amino acids and non-conventional amino acids are described (not limiting to it), for example, in the publication U.S. Pat. No. 6,613,745 (National University of Singapore, 2003) or in the publication "A Textbook of Drug Design and Development", $2^{nd}$ Edition, Harwood Academic Publishers, Singapore.

As another complementary aspect, this invention includes analog compounds to peptides that present the sequences SEQ ID NO: 1, SEQ ID NO: 2, SEQ ID NO: 3 and SEQ ID NO: 4, characterized by being purified or in their pure form.

According to this invention, the term "purified" corresponds to compounds substantially free from contaminants arising from cellular components, other constituents of the venom, medium culture or other materials such as reagents used in the chemical synthesis of the "compounds". Preferably, "purified compounds" are in a quantity greater than 50% of the dry mass of the mixture, more preferably, in a quantity greater than 90% of the dry mass of the mixture, particularly greater than 95%.

As the second main independent aspect, the present invention includes pharmaceutical compositions characterized by containing one or more pharmaceutically acceptable carriers or diluents and one or more compounds that contain the sequences SEQ ID NO: 1, SEQ ID NO: 2, SEQ ID NO: 3, SEQ ID NO: 4, their salts, solvates or analog compounds, preferentially purified.

Examples of pharmaceutical compositions included in this invention are, for instance, solutions, suspensions, pastes, capsule gels, tablets, powders, granules, lyophils, controlled release systems, microparticles, micro or nanospheres, liposomes and organic coatings associated formulations, etc. Possible administration routes for pharmaceutical compositions included in this invention are: oral, intramuscular, intravenous, subcutaneous, topical, pulmonary, intranasal, buccal, rectal, sublingual, intradermic, intraperitoneal, intrathecal, etc., in forms of immediate, delayed, prolonged or controlled release. Examples of pharmaceutical forms, carriers, diluents and administration routes included in this invention are described (not limiting to), for example, in the book Remington's Pharmaceutical Sciences, 17th ed., Mack Publishing Company, Easton, Pa., USA.

As a complementary aspect, this invention also includes pharmaceutical compositions characterized by containing one or more active ingredients in association with analog compounds to peptides that present the sequences SEQ ID NO: 1, SEQ ID NO: 2, SEQ ID NO: 3 and SEQ ID NO: 4, in the same dosage unit or in the form of kits.

As another specific aspect, when the compositions are liquids, semi-solids, or in dry forms for reconstitution, these contain a water-based diluent. As another specific aspect, the compositions can be for oral administration, presenting advantage over injectable compositions, regarding the patient comfort using these administration routes and treatment acceptability.

As the third main independent aspect, this invention includes the use of one or more compounds that contain the sequences SEQ ID NO: 1, SEQ ID NO: 2, SEQ ID NO: 3, SEQ ID NO: 4, their salts, solvates or analog compounds, preferably purified or pure, in the preparation of analgesic pharmaceutical compositions or useful in the treatment, diagnosis or prevention of conditions modulated by opioid receptors.

As a specific aspect, this invention includes the use of one or more compounds that contain the sequences SEQ ID NO: 1, SEQ ID NO: 2, SEQ ID NO: 3, SEQ ID NO: 4, their salts, solvates or analog compounds, preferably purified or pure, in the preparation of compositions with agonist or antagonist properties, direct or indirect, of opioid receptors, particularly kappa opioid receptors.

As another specific aspect, this invention includes the use of one or more compounds containing the sequences SEQ ID NO: 1, SEQ ID NO: 2, SEQ ID NO: 3, SEQ ID NO: 4, their salts, solvates or analog compounds, preferably purified or pure, as analgesic substances, particularly in pharmaceutical compositions for oral administration and/or compounds with long lasting analgesic effects up to 5 days after the administration.

As another specific aspect, this invention also includes the use of one or more compounds containing the sequences SEQ ID NO: 1, SEQ ID NO: 2, SEQ ID NO: 3, SEQ ID NO: 4, their salts, solvates or analog compounds, preferably purified or pure, for the preparation of compositions useful in the treatment, diagnosis or prevention of acute or chronic pain, including cancer pain, neuropathic pain like trigeminal neuralgia, migraine, sympathetic dystrophy, post-herpetic neuralgia, phantom limb pain, post-cerebralvascular accident (stroke), diabetic neuropathy, neoplasia-associated pains, fibromyalgia, dental pain, dysmenorrhea, renal, menstrual or biliary colic, joint pains, arthritis including rheumatoid arthritis or degenerative arthritis, intra-ocular hypertension, post-arthroscopy pain, post-laparoscopy gynecological pain, pain produced by percutaneous nephrolithotomy, radical retropubic post-prostatectomy pain, post-thoracotomy pain, post-tonsillectomy pain in pediatric patients, post-hysterectomy pain, cesarean post-operation or burns pains, cocaine or opioid dependence, cellular proliferation, small cell pulmonary carcinoma, depression and psychosis, inflammation, associated conditions due to increase of angiogenesis, wounds, coronary ischemic diseases, Parkinson's disease and dyskinesias, hepatic encephalopathy, cognitive diseases, Alzheimer's disease, itch due to hepatic cholestasis or hyperinsulinemia in women with polycystic ovary.

As the fourth main independent aspect, this invention includes methods for treating, diagnosing and preventing painful conditions or conditions mediated by opioid receptors with the use of one or more compounds containing the sequences SEQ ID NO: 1, SEQ ID NO: 2, SEQ ID NO: 3, SEQ ID NO: 4, their salts, solvates or analog compounds, preferably purified or pure.

As a specific aspect, this invention includes methods for treating, diagnosing and preventing conditions modulated by opioid receptors, with the use of one or more compounds containing the sequences SEQ ID NO: 1, SEQ ID NO: 2, SEQ ID NO: 3, SEQ ID NO: 4, with direct or indirect, agonist or antagonist properties, on opioid receptors, particularly kappa opioid receptors.

As another specific aspect, this invention includes methods for treating, diagnosing and preventing painful conditions characterized by the use of one or more compounds containing the sequences SEQ ID NO: 1, SEQ ID NO: 2, SEQ ID NO: 3, SEQ ID NO: 4, by oral administration route and/or with long lasting analgesic effect pharmaceutical compositions up to 5 days after the administration.

As another specific aspect, this invention includes methods for treating, diagnosing and preventing, using one or more compounds containing the sequences SEQ ID NO: 1, SEQ ID NO: 2, SEQ ID NO: 3, SEQ ID NO: 4, for conditions such as acute or chronic pain, including cancer pain, neuropathic pain like trigeminal neuralgia, migraine, sympathetic dystrophy, post-herpetic pain, ghost limb pain, post cerebralvascular accident (stroke), diabetic neuropathy, neoplasia-associated pains, fibromyalgia, dental pain, dysmenorrhea, renal, menstrual or biliary colic, joint pains, arthritis including rheumatoid arthritis or degenerative arthritis, intra-ocular hypertension, post-arthroscopy pain, post-laparoscopy gynecological pain, pain produced by percutaneous nephrolithotomy, radical retropubic post-prostatectomy pain, post-thoracotomy pain, post-tonsillectomy pain in pediatric patients, post-hysterectomy pain, cesarean post-operation or burn pains, cocaine or opioid dependence, cellular proliferation, small cell pulmonary carcinoma, depression and psychosis, inflammation, associated conditions due to increase of angiogenesis activity, wounds, coronary ischemic diseases, Parkinson's disease and dyskinesias, hepatic encephalopathy, cognitive diseases, Alzheimer's disease, itch due to hepatic cholestasis or hyperinsulinemia in women with polycystic ovary.

As the fifth main independent aspect, this invention includes production and purification processes of analog compounds to peptides containing the sequences SEQ ID NO: 1, SEQ ID NO: 2, SEQ ID NO: 3, SEQ ID NO: 4, their salts, solvates or analog compounds.

As a specific aspect, this invention includes production processes of compounds containing the sequence SEQ ID NO 4, their salts and analog compounds, containing an intramolecular disulfide bridge between the cysteine residues in positions 7 and 14, characterized by involving oxidation stage of the sulphydryls of positions 7 and 14, with an enzymatic agent or through oxidation with oxidizing agents (such as iodine, air, oxygen or potassium ferricyanide) or even characterized by involving a purification stage of a compound containing in its structure the amino acid sequence.

Cys-Glx-Gly-R5-Ser-R6-Pro-Cys (SEQ ID NO: 5)

wherein
R5=Glx or Asx,
R6=Glx or Lys
and wherein the cysteine residues are linked by an intramolecular disulfide bridge.

As another specific aspect, this invention includes production processes of compounds containing the sequences SEQ ID NO: 1, SEQ ID NO: 2, SEQ ID NO: 3, SEQ ID NO: 4, their salts, solvates or analog compounds, purified, through the purification of mixtures of compounds of synthetic, semi-synthetic or biological origin; for example: the crude venom of *Crotalus durissus terrificus* snakes or even cell cultures, of recombinant microorganisms, or their respective lysates, using selective precipitation and/or separation by chromatographic processes.

In the case of selective precipitation, the use of trifluoroacetic acid solutions in acetonitrile and water mixtures, particularly in concentration of approximately 0.1% of trifluoroacetic acid in acetonitrile and water mixtures in a proportion of approximately 1:2 is particularly useful.

For separation by chromatography, the use of HPLC columns with reverse phase and the application of mobile phase with gradient concentration, and the use of trifluoroacetic acid solutions in acetonitrile and water as mobile phase is particularly useful.

Examples of synthesis and purification processes of analog compounds to peptides with sequence SEQ ID NO: 1, SEQ ID NO: 2, SEQ ID NO: 3, SEQ ID NO: 4 includes, for example (not limiting to), those described in the publication "Amino Acid and Peptide Synthesis", $2^{nd}$ Edition, Oxford University Press, Bath, Great Britain; Principles of Biochemistry, $3^{rd}$ Edition, Worth Publishers, USA.

As the sixth main independent aspect, this invention includes methods of identification of compounds that mimic the analgesic activity of a peptide that has the amino acid sequence SEQ ID NO: 2 or SEQ ID NO: 3.

As the sixth specific aspect, this invention includes methods for identifying compounds that mimic the analgesic activity of a peptide that has the amino acid sequence SEQ ID NO: 1, SEQ ID NO: 2, SEQ ID NO: 3, SEQ ID NO: 4 characterized by including the stages of:

a) evaluation of the biologic activity of a peptide having the amino acid sequence SEQ ID NO: 1, SEQ ID NO: 2, SEQ ID NO: 3, SEQ ID NO: 4, for determining its analgesic activity, b) evaluation of the biologic activity of a test compound (control), for determining analgesic activity and c) compare the results obtained for the biologic activity of SEQ ID NO: 1, SEQ ID NO: 2, SEQ ID NO: 3, SEQ ID NO: 4 with the results obtained the test compound (control).

or a) inserting a peptide with the amino acid sequence SEQ ID NO: 1, SEQ ID NO: 2, SEQ ID NO: 3, SEQ ID NO: 4, marked, in contact with a test sample, b) adding a test compound to the test sample in contact with a peptide with the amino acid sequence SEQ ID NO: 1, SEQ ID NO: 2, SEQ ID NO: 3, SEQ ID NO: 4, marked, and c) evaluate the peptide link of the amino acid sequence SEQ ID NO: 1, SEQ ID NO: 2, SEQ ID NO: 3, SEQ ID NO: 4, marked, with the test sample.

Examples of methods of identification of compounds that mimic the analgesic activity of peptides are described (without limitation), for example, in the publication U.S. Pat. No. 5,877,026 (Lampe R. A., 1999).

This invention is complementarily illustrated by the following non-limiting experimental examples:

EXAMPLE 1

Isolation and Purification of ENPAK-k from the Venom of *Crotalus durissus terrificus*

20 mg lyophilized unrefined venom from *Crotalus durissus terrificus* snakes (furnished by the Herpetology Laboratory of the Butantan Institute) were diluted in 1.5 ml of a 1:2 acetonitrile/water solution containing 0.1% of trifluoroacetic acid (TFA). The supernatant was fractioned through a Sep-Pak $C_{18}$ (2 g, 12 cc, Millipore) column and eluated in different concentrations of acetonitrile/water (containing 0.1% of TFA). This procedure was repeated 60 times and the pool obtained from the fractions of each acetonitrile/water concentration was lyophilized.

The fraction obtained from the eluation of 20% of acetonitrile/water (containing 0.1% of trifluoroacetic acid—TFA) was dissolved in water and subjected to an HPLC reverse-phase column (Shimadzu Co. Ltd.), using a CAPCELL PAK $C_{18}$, 6 mm×150 mm column (Shiseido Co. Ltd.) on linear gradient from 15% to 35% of acetonitrile/water (containing 0.1% of TFA), with flow of 1 ml/min for 25 minutes at room temperature. The fraction obtained from the retention time of 10.7 minutes was collected with UV spectrophotometric monitoring, in the wavelength at 215 nm.

The fraction obtained was again subjected to HPLC, using a CAPCELL PAK $C_{18}$, 6 mm×150 mm column in isocratic of 15% of acetonitrile/water (containing 0.1% of TFA), with flow of 1 ml/min at room temperature, and the fraction obtained from the retention time of 14 minutes was collected with UV spectrophotometric monitoring, in the wavelength at 215 nm. The resulting fraction demonstrated high grade of purity in MALDI-TOF mass spectrometry using Ettan MALDI-Tof/Pro (Amersham Biosciences), with molecular ionic peak $[(M+H)^+$, monoisotopic] at m/z 1534.6. This fraction was lyophilized and denominated ENPAK-k in this invention.

EXAMPLE 2

Determination of Amino Acid Sequence of ENPAK-k

The amino acid sequence of the resulting peptide was determined by mass spectrometry, since the sequence was not obtained through Edman's degradation, due to N-terminal blocking.

Initially, the disulfide bridge was reduced and alkylated. An aliquot of the resulting pure ENPAK-k was dissolved in 10 μl of water. To this solution was added 10 μl of 5 mM of dithiothreitol in 25 mM of ammonium bicarbonate buffer, and the solution was maintained at 60° C. for 30 min. After cooling at room temperature, 10 μl of a 55 mM of iodoacetamide solution in 25 mM of ammonium bicarbonate buffer was added and then maintained at room temperature for 30 minutes. The MALDI-TOF MS of this product showed molecular ionic peak $[(M+H)^+$, monoisotopic] at m/z 1650.7, demonstrating that there is a disulfide bridge in the natural peptide.

The reduced-alkylated peptide sequence was analyzed through ESI tandem mass spectrometry using Q-Tof Ultima™ (Micromass). A tandem mass spectrum from the double charged ion $[(M+2H)^{2+}$, monoisotopic] at m/z 825.90 provided series of b and y ions, giving a sequence of 14 hypothetical amino acid residues represented by: pGlu-Phe-Ser-Pro-Glu-Asn-Cys-Lys/Gln-Gly-Glu-Ser-Lys/Gln-Pro-Cys, considering the data obtained with the mass spectrometry, wherein pGlu shows pyroglutamate residues, and Lys/Gln implies that it is possible for Lys or Gln in this position. The 2 Cys residues are linked to each other by a disulfide bridge.

Thus, there would be 4 possible sequences SEQ ID NO: 2, SEQ ID NO: 3, SEQ ID NO: 6, SEQ ID NO: 7 that would correspond to ENPAK-k. The following sequences were obtained:

```
                                                            (SEQ ID NO: 2)
pGlu-Phe-Ser-Pro-Glu-Asn-Cys-Gln-Gly-Glu-Ser-Gln-Pro-Cys
                                                            (SEQ ID NO: 3)
pGlu-Phe-Ser-Pro-Glu-Asn-Cys-Gln-Gly-Glu-Ser-Lys-Pro-Cys
                                                            (SEQ ID NO: 6)
pGlu-Phe-Ser-Pro-Glu-Asn-Cys-Lys-Gly-Glu-Ser-Gln-Pro-Cys
                                                            (SEQ ID NO: 7)
pGlu-Phe-Ser-Pro-Glu-Asn-Cys-Lys-Gly-Glu-Ser-Lys-Pro-Cys
```

Wherein the cysteine residues are linked by an intramolecular disulfide bridge and the amino acids are represented by the three-letter code corresponding to, respectively:

pGlu=pyroglutamate
Phe=phenylalanine
Ser=serine
Pro=proline
Glu=glutamic acid
Asn=asparagine
Cys=cysteine
Gln=glutamine
Lys=lysine
Gly=glycine These amino acid sequences, when compared to known protein sequences, deposited in the Swiss Prot database, showed that the peptide SEQ ID NO: 2 has identity with the amino acid sequence of the C-terminal portion of crotapotin, non-toxic acidic subunit of the crotoxin from the snake venom of the *Crotalus durissus terrificus* species (Faure G, Guillaume J L, Camoin L, Saliou B, Bon C. Biochemistry, 1991, 13, 8074-8083); except the fact that the cysteine residues in the C-terminal portion of the crotapotin do not present intramolecular disulfide bridge like the peptide SEQ ID) NO: 2:

C-terminal portion of the crotapotin, non-toxic acidic subunit from the crotoxin of the snake venom of the *Crotalus durissus terrificus* species:

```
                                                  (SEQ ID NO: 8)
pGlu-Phe-Ser-Pro-Glu-Asn-Cys-Gln-Gly-Glu-Ser-Gln-

Pro-Cys
```

EXAMPLE 3

Synthesis of Peptides SEQ ID NO: 2, SEQ ID NO: 3, SEQ ID NO: 6, SEQ ID NO: 7, as Non-Limiting Example The peptides SEQ ID NO: 2, SEQ ID NO: 3, SEQ ID NO: 6 and SEQ ID NO: 7 were obtained through the manual peptide synthesis in solid phase, through the Fmoc strategy, using H-Cys(Trt)-2-ClTrt resin as solid support.

Each one of the synthesized peptides was then cleaved from the resin through the addition of acetic/trifluoroethanol/dichloromethane (1:1:8) at room temperature, for 1 hour, followed by deprotection through a solution of TFA/thioanisol/1,2-ethanedithiol (94:5:1), also at room temperature, for 2 hours. After the treatments, ether was added to the TFA solution to precipitate the peptides. The precipitate was washed 3 times with ether to obtain the SH-free unrefined peptides. The disulfide bridge was formed by the treatment with 0.1 M solution of methanol and iodine at room temperature, for 30 minutes, followed by the addition of an aqueous solution of 0.1 M ascorbic acid. Afterwards, the obtained unrefined peptides were purified by reverse phase HPLC using YMC-Pak ODS, 20×150 mm (Yamamura Kagaku Co. Ltd.) in linear gradient from 15% to 35% of acetonitrile/water containing 0.1% TFA with flow of 8 ml/min for 25 minutes, at room temperature. The comparison of the resulting synthetic peptides:

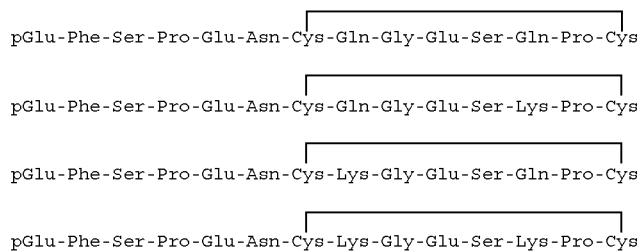

```
                                                            (SEQ ID NO: 2)
pGlu-Phe-Ser-Pro-Glu-Asn-Cys-Gln-Gly-Glu-Ser-Gln-Pro-Cys (SEQ ID NO: 3)
pGlu-Phe-Ser-Pro-Glu-Asn-Cys-Gln-Gly-Glu-Ser-Lys-Pro-Cys (SEQ ID NO: 6)
pGlu-Phe-Ser-Pro-Glu-Asn-Cys-Lys-Gly-Glu-Ser-Gln-Pro-Cys (SEQ ID NO: 7)
pGlu-Phe-Ser-Pro-Glu-Asn-Cys-Lys-Gly-Glu-Ser-Lys-Pro-Cys
``` wherein the cysteine residues are linked by an intramolecular disulfide bridge,
with the natural ENPAK-k peptide, in HPLC and mass spectrometry, demonstrated that the peptide SEQ ID NO: 2 is identical to the natural ENPAK-k. Complementarily, the peptide SEQ ID NO: 2 showed the same analgesic activity as the natural ENPAK-k. The peptide SEQ ID NO: 3 also demonstrated analgesic activity, while the other 2 peptides (SEQ ID NO: 6 and SEQ ID NO: 7) showed inactivity in similar conditions.

Based on molecular modeling studies of the sequences SEQ ID NO: 2 and SEQ ID NO: 3, other important sequences for this invention were proven:

```
                                              (SEQ ID NO: 1)
Xaa-R1-Ser-R2-R3-R4-Cys-Glx-Gly-R5-Ser-R6-Pro-Cys
``` particularly

```
                                              (SEQ ID NO: 4)
Xaa-R1-Ser-R2-R3-R4-Cys-Glx-Gly-R5-Ser-R6-Pro-Cys
``` wherein:
Xaa is always pyroglutamate,
R1=Phe or Trp or Tyr or Leu or Thr,
R2=Pro or Arg,
R3=Glx or Asx or Gly,
R4=Asn or Gln or Leu,
R5=Glx or Asx,
R6=Glx or Lys,

EXAMPLE 4

Identification of the Analgesic Fraction in Each Purification Stage: Rat Paw Pressure Test For evaluating the pain sensitivity of animals, male Wistar Rats, weighing between 170-190 g, provided by Biotério Central of the Butantan Institute, were used. The animals were maintained in the laboratory, with light/dark cycle of 12/12 hours and controlled temperature at 22±1° C., with access to water and food ad libitum. The protocol used was approved by the Institutional Animal Care Committee at the Butantan Institute (CEUAIB) under the protocol number 019/2000.

For evaluation of pain sensitivity, rat paw pressure test was used (Analgesy-Meter Ugo Basile®, Italy), performed according to the method described by Randall & Selitto (Randall L. O. and Selitto J. J. Arch. Intern. Pharmacodyn. 111: 209-219, 1957).

In this test, a force in grams (g), with increasing magnitude (16 g/s), is continuously applied on the dorsal surface of one of the hind paws of the rat and interrupted when the animal reacts "withdrawing" the paw. In this model, the pain threshold is represented as the force (g) necessary for the induction of the reaction. This test was applied before (initial measurement) and 3 hours after (final measurement) the induction of hyperalgesia.

For the induction of hyperalgesia, a stock solution of prostagiandin $E_2$ ($PGE_2$) was prepared, dissolving 500 μg of $PGE_2$ in 1 ml of ethanol. At the moment of use, this stock solution was rediluted in sterile saline. The dose of prostaglandin used was 100 ng in 100 μl of saline, administered by i.pl. route. Hyperalgesia was evaluated 3 hours after $PGE_2$ injection.

At each step of purification, the material obtained was diluted. in a volume of 11 ml of saline. Each animal received 2 ml of this solution, administered by oral route, immediately before the induction of hyperalgesia. Animals administered with saline were used as controls.

EXAMPLE 5

Evaluation of the Effectiveness and Duration of the Antinociceptive Effect of the Isolated Natural Peptide ENPAK-k from *Crotalus durissus terrificus* Venom The natural peptide, ENPAK-k, isolated from the purification of 60 mg of crude venom, in accordance with EXAMPLE 1, was diluted in a volume of 33 ml of saline. Each animal received 2 ml of this solution, administered orally (p.o.), immediately before the induction of hyperalgesia. Animals that received saline, orally, were used as controls.

For evaluation of pain sensitivity, rat paw pressure test was used. The pain threshold, represented by the force (in grams) necessary for withdrawing the paw, was determined before (time 0) and 3, 72 and 120 hours (final measurements) after the treatment, p.o., with the natural peptide (ENPAK-k) or saline (control group). Prostaglandin (100 ng/paw), used as hyperalgesic agent, was injected 3 hours before every final measurement. The data presented in Table 1 represent the mean±S.E.M of 5 animals per group.

TABLE 1

EFFECTIVENESS AND DURATION OF THE ANTINOCICEPTIVE EFFECT OF THE NATURAL PEPTIDE (ENPAK-k) ISOLATED FROM Crotalus durissus terrificus VENOM.

| Treatment | 0 h IM (g) ± S.E.M. | 3 h FM (g) ± S.E.M. | 72 h FM (g) ± S.E.M. | 120 h FM (g) ± S.E.M. |
|---|---|---|---|---|
| Saline | 76 ± 1.00 | 56 ± 1.87* | 58 ± 1.22* | 57 ± 1.22* |
| Natural Peptide | 77 ± 2.00 | 118 ± 2.55*# | 113 ± 2.55*# | 112 ± 3.39*# |

*$p < 0.05$ significantly different from means values of initial measurement
$p < 0.05$ significantly different from means values of control group (saline).
IM = initial measurement;
FM = final measurement;
g = weight in grams This example shows the effectiveness and the long lasting antinociceptive effect of the natural peptide ENPAK-k isolated from Crotalus durissus terrificus snake venom.

EXAMPLE 6

Dose-Response Curves of the Analgesic Activity of the Synthetic Peptide SEQ ID NO: 2 in the Prostaglandin E$_2$-Induced Hyperalgesia Model as Non-Limiting Example The synthetic peptide SEQ ID NO: 2, in different doses, was diluted in saline, and administered by different routes, immediately before the induction of hyperalgesia. Animals that received saline through the same routes were used as controls.

For the induction of hyperalgesia, prostaglandin E$_2$, at the dose of 100 ng/paw was administered by intraplantar route (i.pl.). Hyperalgesia was evaluated before (initial measurement—IM) and 3 hours after (final measurement—FM) PGE$_2$ injection.

For pain sensitivity evaluation, the rat paw pressure test was used. The pain threshold, represented by the force (in grams) necessary to induce the withdrawal of the paw, was determined before (initial measurement) and 3 hours after (final measurement) the intraplantar injection of prostaglandin E$_2$ (100 ng/leg). The synthetic peptide was administered, before hyperalgesic stimulus, by the following routes and doses:

A) Oral route, in a volume of 2 ml, in the doses of 0.0016; 0.008; 0.04; 0.2; 1; 5 and 25 µg/kg, immediately before the induction of hyperalgesia (table 2).
B) Intraplantar route, in a volume of 50 µl, in the doses of 0.00000256; 0.0000128; 0.00032 and 0.0016 µg/paw, immediately before the induction of hyperalgesia (table 3).
C) Intravenous route, in a volume of 200 µl, in the doses of 0.0000128, 0.000064, 0.00032, 0.0016 and 0.008 µg/kg, immediately before the induction of hyperalgesia (table 4).
D) An additional group was tested, using morphine as positive control. Morphine was administered, orally, in doses of 0.004; 0.2; 1 and 5 µg/kg (table 5).

Saline, administered by the respective routes, was used as control in all the experiments.

The results were analyzed comparing the means of the initial and final measurements or, when determined, comparing the means obtained in the different experimental groups. The data were used to determine ED$_{50}$, ED$_{60}$ and ED 90.

In Tables 2, 3, 4 and 5: IM=initial measurement; FM=final measurement; g=weight in grams; peptide doses are represented in µg/kg, when administered orally and intravenously, or in µg/paw, when administered by intraplantar route. The data represent the means±S.E.M of 5 animals per group.

TABLE 2

DOSE-RESPONSE CURVE OF THE ANALGESIC ACTIVITY OF THE SYNTHETIC PEPTIDE SEQ ID NO: 2, ADMINISTERED BY ORAL ROUTE, IN THE PROSTAGLANDIN E$_2$-INDUCED HYPERALGESIA MODEL.

| Treatments | IM (g) ± S.E.M | FM (g) ± S.E.M |
|---|---|---|
| Saline (p.o.) + PGE$_2$ (i.pl.) | 77 ± 1.34 | 56 ± 1.30* |
| Peptide (0.0016, p.o.) + PGE$_2$ (i.pl.) | 78 ± 1.22 | 64 ± 1.00* |
| Peptide (0.008, p.o.) + PGE$_2$ (i.pl.) | 79 ± 1.25 | 71 ± 2.39# |
| Peptide (0.04, p.o.) + PGE$_2$ (i.pl.) | 77 ± 1.22 | 75 ± 1.87# |
| Peptide (0.2, p.o.) + PGE$_2$ (i.pl.) | 77 ± 2.00 | 84 ± 1.87# |
| Peptide (1.0, p.o.) + PGE$_2$ (i.pl.) | 77 ± 2.00 | 108 ± 2.00*# |
| Peptide (5.0, p.o.) + PGE$_2$ (i.pl.) | 78 ± 2.00 | 130 ± 1.58*# |
| Peptide (25.0, p.o.) + PGE$_2$ (i.pl.) | 79 ± 1.87 | 133 ± 3.39*# |

*$p < 0.05$ significantly different from means values of initial measurement
$p < 0.05$ significantly different from means values of control group (saline).

These results showed the potent analgesic effect of the synthetic peptide SEQ ID NO: 2, administered orally, in the PGE$_2$-induced hyperalgesia model. For determination of 50, 60 and 90% effective doses, the data were analyzed determining the percentage of decrease of the pain threshold (hyperalgesia), comparing the final and initial measurements, followed by the determination of the percentage of reversal of hyperalgesia, comparing the treated (peptide) and control (saline) groups. These data were analyzed using CurveExpert 1.3 program. The results demonstrated that 50, 60 and 90% effective doses of the peptide, in this example, were 0.004146; 0.006348 and 0.02106 µg/kg, respectively. It is important to note that only the doses of 0.0016; 0.008; 0.04 and 0.2 were used for the determination of the effective doses.

TABLE 3

DOSE-RESPONSE CURVE OF THE ANALGESIC ACTIVITY OF THE SYNTHETIC PEPTIDE SEQ ID NO: 2, ADMINISTERED BY INTRAPLANTAR ROUTE IN THE PROSTAGLANDIN $E_2$-INDUCED HYPERALGESIA MODEL.

| Treatments | IM (g) ± S.E.M | FM (g) ± S.E.M |
| --- | --- | --- |
| Saline (i.pl.) + PGE2 (i.pl.) | 75 ± 1.83 | 40 ± 3.10* |
| Peptide (0.00000256) (i.pl.) + PGE2 (i.pl.) | 72 ± 1.12 | 57 ± 5.34* |
| Peptide (0.0000128) (i.pl.) + PGE2 (i.pl.) | 71 ± 2.39 | 62 ± 3.22# |
| Peptide (0.00032) (i.pl.) + PGE2 (i.pl.) | 67 ± 2.35 | 60 ± 3.25# |
| Peptide (0.0016) (i.pl.) + PGE2 (i.pl.) | 72 ± 1.84 | 67 ± 1.12# |

*$p < 0.05$ significantly different from means values of initial measurement
$p < 0.05$ significantly different from means values of control group (saline).

These results showed the potent analgesic effect of the synthetic peptide SEQ ID NO: 2, administered by intraplantar route, in the $PGE_2$-induced hyperalgesia model. For determination of 50, 60 and 90% effective doses, the data were analyzed determining the percentage of decrease of the pain threshold (hyperalgesia), comparing the final and initial measurements, followed by the determination of the percentage of reversal of hyperalgesia, comparing the treated (peptide) and control (saline) groups. These data were analyzed using CurveExpert 1.3 program. The results demonstrated that 50, 60 and 90% effective doses of the peptide, in this example, were 0.000002327; 0.000004904 and 0.0028758 µg/kg, respectively.

TABLE 4

DOSE-RESPONSE CURVE OF THE ANALGESIC ACTIVITY OF THE SYNTHETIC PEPTIDE SEQ ID NO: 2, ADMINISTERED BY INTRAVENOUS ROUTE IN THE PROSTAGLANDIN $E_2$-INDUCED HYPERALGESIA MODEL.

| Treatments | IM (g) ± S.E.M | FM (g) ± S.E.M |
| --- | --- | --- |
| Saline + PGE2 (i.pl.) | 72 ± 1.83 | 44 ± 2.67* |
| Peptide (0.0000128) (i.v.) + PGE2 (i.pl.) | 70 ± 2.05 | 54 ± 3.04* |
| Peptide (0.000064) (i.v.) + PGE2 (i.pl.) | 68 ± 1.44 | 54 ± 2.39 |
| Peptide (0.00032) (i.v.) + PGE2 (i.pl.) | 72 ± 1.84 | 63 ± 5.16# |
| Peptide (0.0016) (i.v.) + PGE2 (i.pl.) | 74 ± 0.92 | 67 ± 2.35# |
| Peptide (0.008) (i.v.) + PGE2 (i.pl.) | 69 ± 2.26 | 73 ± 4.74# |

*$p < 0.05$ significantly different from means values of initial measurement
$p < 0.05$ significantly different from means values of control group (saline).

These results showed the potent analgesic effect of the synthetic peptide SEQ ID NO: 2, administered by intravenous route, in the $PGE_2$-induced hyperalgesia model. For determination of 50, 60 and 90% effective doses, the data were analyzed determining the percentage of decrease of the pain threshold (hyperalgesia), comparing the final and initial measurements, followed by the determination of the percentage of reversal of hyperalgesia, comparing the treated (peptide) and control (saline) groups. These data were analyzed using CurveExpert 1.3 program. The results demonstrated that 50, 60 and 90% effective doses of the peptide, in this example, were 0.0000458; 0.0002144 and 0.002701 µg/kg, respectively.

TABLE 5

DOSE-RESPONSE CURVE OF THE ANALGESIC ACTIVITY OF MORPHINE, ADMINISTERED BY ORAL ROUTE, IN THE PROSTAGLANDIN $E_2$-INDUCED HYPERALGESIA MODEL.

| Treatments | IM (g) ± S.E.M. | FM (g) ± S.E.M |
| --- | --- | --- |
| Saline (p.o.) + PGE2 (i.pl.) | 77 ± 2.55 | 59 ± 1.87* |
| Morphine (0.004) (p.o.) + PGE2 (i.pl.) | 77 ± 1.22 | 69 ± 1.87# |
| Morphine (0.2) (p.o.) + PGE2 (i.pl.) | 76 ± 1.87 | 70 ± 1.58# |
| Morphine (1) (p.o.) + PGE2 (i.pl.) | 78 ± 1.22 | 85 ± 1.58# |
| Morphine (5) (p.o.) + PGE2 (i.pl.) | 78 ± 1.22 | 109 ± 1.87*# |

Morphine dose = µg/kg
*$p < 0.05$ significantly different from means values of initial measurement
$p < 0.05$ significantly different from means values of control group (saline).

These results showed the analgesic effect of morphine, administered by oral route, in the $PGE_2$-induced hyperalgesia model. For determination of 50, 60 and 90% effective doses, the data were analyzed determining the percentage of decrease of the pain threshold (hyperalgesia), comparing the final and initial measurements, followed by the determination of the percentage of reversal of hyperalgesia, comparing the treated (peptide) and control (saline) groups. These data were analyzed using CurveExpert 1.3 program. The results demonstrated that 50, 60 and 90% effective doses of the peptide, in this example, were 0.0551516; 0.1.00504 and 0.326728 µg/kg, respectively.

EXAMPLE 7

Evaluation of the Duration of the Antinociceptive Effect of the Synthetic Peptide SEQ ID NO: 2 in the Prostaglandin $E_2$-Induced Hyperalgesia Model After demonstrating the antinociceptive effect of the synthetic peptide in the prostaglandin $E_2$-induced hyperalgesia model, the duration of this effect was investigated. For evaluation of pain sensitivity, rat paw pressure test was used. The pain threshold, represented by the force (in grams) necessary for the reaction of withdrawal of the paw, was determined before (initial measurement) and 24, 48, 72, 96, 120 and 144 hours after (final measurements) the oral administration of the synthetic peptide (1 µg/kg) or saline (control). $PGE_2$, in the dose of 100 ng/paw, was administered in the different groups, 3 hours before each final measurement (Table 6).

TABLE 6

DURATION OF THE ANTINOCICEPTIVE EFFECT OF THE SYNTHETIC PEPTIDE SEQ ID NO: 2 IN THE $PGE_2$-INDUCED HYPERALGESIA MODEL.

| | Time after peptide administration (hours) | | | | | | |
|---|---|---|---|---|---|---|---|
| | 0 | 24 | 48 | 72 | 96 | 120 | 144 |
| Treatments | IM (g) ± S.E.M | FM (g) ± S.E.M | FM (g) ± S.E.M | FM (g) ± S.E.M | FM (g) ± S.E.M | FM (g) ± S.E.M | FM (g) ± S.E.M |
| Saline | 78 ± 1.66 | 58 ± 1.66* | 62 ± 1.66* | 58 ± 3.33* | 56 ± 1.87* | 57 ± 2.55* | 57 ± 1.22* |
| Peptide | 79 ± 1.00 | 126 ± 3.32*# | 121 ± 1.87*# | 111 ± 4.3*# | 117 ± 2.5*# | 130 ± 2.24*# | 59 ± 2.39* |

*p < 0.05 significantly different from means values of initial measurement
p < 0.05 significantly different from means values of control group (saline).
IM = initial measurement;
FM = final measurement;
g = weight in grams The results demonstrated that the antinociceptive effect of the peptide was detected up to 120 hours after one single administration.

EXAMPLE 8

Evaluation of the Participation of Opioid Receptors in the Antinociceptive Effect of the Synthetic Peptide SEQ ID NO: 2, in the $PGE_2$-Induced Hyperalgesia Model For evaluation of pain sensitivity, rat paw pressure test was used. Pain threshold, represented by the force (in grams) necessary to induce the withdrawal of the paw was determined before (initial measurement, IM) and 3 hours after (final measurement, FM) the intraplantar injection of prostaglandin $E_2$ (100 ng/paw). The synthetic peptide (1 µg/kg) or saline (control group), were administered orally, immediately before the hyperalgesic stimulus ($PGE_2$). ICI174,864—ICI (10 µg/paw), a delta opioid receptor antagonist, nor-Binalthorphimine—BNI (50 µg/leg), a kappa opioid receptor antagonist and CTOP (20 µg/leg), a mu opioid receptor antagonist were administered by intraplantar route (i.pl.) concomitantly with $PGE_2$ injection (Table 7). The data represent the means±S.E.M of 5 animals per group.

In addition, kappa and delta opioid receptors antagonists were also tested in the antinociception induced by the peptide in the dose of 5 µg/kg (Table 8). The data represent the means±S.E.M. of 5 animals per group.

TABLE 7

EVALUATION OF THE PARTICIPATION OF OPIOID RECEPTORS IN THE ANTINOCICEPTIVE EFFECT OF THE SYNTHETIC PEPTIDE (1 µg/kg) IN THE PROSTAGLANDIN $E_2$-INDUCED HYPERALGESIA MODEL

| Treatments | IM (g) ± S.E.M. | FM (g) ± S.E.M. |
|---|---|---|
| Saline + $PGE_2$ | 78 ± 1.44 | 56 ± 1.25* |
| Peptide + $PGE_2$ | 77 ± 1.22 | 111 ± 3.32*# |
| Peptide + $PGE_2$ + ICI174,864 | 78 ± 1.22 | 114 ± 1.00*# |
| Peptide + $PGE_2$ + nor-Binalthorphimine | 77 ± 1.22 | 56 ± 1.87* |
| Peptide + $PGE_2$ + CTOP | 77 ± 1.22 | 114 ± 1.87*# |
| Saline + $PGE_2$ + ICI174,864 | 75 ± 2.04 | 57 ± 3.22* |
| Saline + $PGE_2$ + nor-Binalthorphimine | 72 ± 1.44 | 56 ± 1.25* |
| Saline + $PGE_2$ + CTOP | 74 ± 2.39 | 56 ± 2.39* |

* p < 0.05 significantly different from means values of initial measurement
p < 0.05 significantly different from means values of control group (saline).
IM = initial measurement;
FM = final measurement;
g = weight in grams These data indicate that in the $PGE_2$-induced hyperalgesia model, kappa opioid receptors are involved in the antinociceptive effect of the synthetic peptide SEQ ID NO: 2 (1 µg/kg).

TABLE 8

EVALUATION OF THE PARTICIPATION OF OPIOID RECEPTORS IN THE ANTINOCICEPTIVE EFFECT OF THE SYNTHETIC PEPTIDE (5 µg/kg) IN THE PROSTAGLANDIN $E_2$-INDUCED HYPERALGESIA MODEL.

| Treatments | IM (g) ± S.E.M. | FM (g) ± S.E.M. |
|---|---|---|
| Saline + PGE2 | 78 ± 1.44 | 59 ± 2.39* |
| Peptide + PGE2 | 77 ± 1.22 | 147 ± 2.55*# |
| Peptide + PGE2 + nor-BNI | 77 ± 1.05 | 58 ± 2.47* |
| Peptide + PGE2 + ICI174,864 | 77 ± 1.05 | 145 ± 2.89*# |
| Saline + PGE2 + nor-BNI | 72 ± 1.44 | 56 ± 1.25* |
| Saline + PGE2 + ICI174,864 | 75 ± 2.04 | 57 ± 3.22* |

*p < 0.05 significantly different from means values of initial measurement
p < 0.05 significantly different from means values of control group (saline).
IM = initial measurement;
FM = final measurement;
g = weight in grams These data indicate that in the $PGE_2$-induced hyperalgesia model, kappa opioid receptors are involved in the antinociceptive activity of the synthetic peptide SEQ ID NO: 2, even when used in higher dose (5 µg/kg).

EXAMPLE 9

Analgesic Activity of the Synthetic Peptide SEQ ID NO: 2 in the Carrageenin-Induced Hyperalgesia Model as Non-Limiting Example The antinociceptive effect of the synthetic peptide was evaluated in the inflammatory hyperalgesia induced by carrageenin. The rat paw pressure test was applied before (initial measurement) and 3 hours after (final measurement) the carrageenin-induced inflammatory hyperalgesia (200 μg/paw). The synthetic peptide was administered by oral route (2 ml), in the dose of 1 μg/kg, immediately before the induction of hyperalgesia (Table 9). Saline, administered by the same route was used as control. The data represent the means±S.E.M. of 5 animals per group.

TABLE 9

ANTINOCICEPTIVE EFFECT OF THE SYNTHETIC PEPTIDE SEQ ID NO: 2 IN THE CARRAGEENIN-INDUCED HYPERALGESIA MODEL

| Treatments | IM (g) ± S.E.M. | FM (g) ± S.E.M. |
|---|---|---|
| Saline + carrageenin | 77 ± 2.00 | 57 ± 2.00* |
| Peptide + carrageenin | 77 ± 2.00 | 116 ± 1.87*# |

*p < 0.05 significantly different from means values of initial measurement
p < 0.05 significantly different from means values of control group (saline).
IM = initial measurement;
FM = final measurement;
g = weight in grams The results demonstrate that the synthetic peptide is able to induce antinociception also in the inflammatory hyperalgesia model induced by carrageenin.

EXAMPLE 10

Determination of the Participation of Opioid Receptors in the Analgesic Activity of the Synthetic Peptide SEQ ID NO: 2, in the Carrageenin-Induced Hyperalgesia Model As determined in the $PGE_2$ model, the participation of opioid receptors in the antinociceptive effect of the peptide SEQ ID NO: 2 in the carrageenin-induced hyperalgesia (Table 10) was investigated. Therefore, the animals were treated with CTOP, a specific μ receptor antagonist (20 μg/paw), nor-BNI, a specific κ receptor antagonist (50 μg/paw) or with ICI 174.864, a specific δ receptor antagonist (10 μg/paw), injected by i.pl. route concomitantly to carrageenin. Peptide was administered in the dose of 1 μg/kg, orally, immediately before carrageenin. The data represent the means±S.E.M. of 5 animals per group.

TABLE 10

EVALUATION OF THE PARTICIPATION OF OPIOID RECEPTORS IN THE ANTINOCICEPTIVE EFFECT OF THE SYNTHETIC PEPTIDE (1 μg/kg) IN THE CARRAGENIN-INDUCED HYPERALGESIA MODEL.

| Treatments | IM (g) ± S.E.M. | FM (g) ± S.E.M. |
|---|---|---|
| Saline + carrageenin | 75 ± 2.04 | 57 ± 1.44* |
| Peptide + carrageenin | 77 ± 1.22 | 129 ± 1.87*# |
| Peptide + carrageenin + CTOP | 76 ± 1.87 | 126 ± 2.92*# |
| Peptide + carrageenin + nor-BNI | 78 ± 2.00 | 56 ± 1.00* |
| Peptide + carrageenin + ICI174,864 | 77 ± 1.22 | 128 ± 2.00*# |
| Saline + carrageenin + CTOP | 73 ± 1.25 | 49 ± 1.25* |
| Saline + carrageenin + nor-BNI | 72 ± 1.12 | 52 ± 2.79* |
| Saline + carrageenin + ICI174,864 | 72 ± 1.7 | 51 ± 2.47* |

*p < 0.05 significantly different from means values of initial measurement
p < 0.05 significantly different from means values of control group (saline).
IM = initial measurement;
FM = final measurement;
g = weight in grams As observed in the $PGE_2$-induced hyperalgesia model, only kappa opioid receptor antagonist was able to interfere with the antinociceptive effect of the peptide.

EXAMPLE 11

Analgesic Activity of the Synthetic Peptide SEQ ID NO: 2 in Hyperalgesia Induced by the Chronic Constriction of the Sciatic Nerve, a Persistent Pain Model For the induction of neuropathic pain, surgery was performed in the sciatic nerve, in accordance with the method described by Bennett, G. J and Xie, Y. K. (Pain, 33:87-107, 1988). The animals were anesthetized with halothane. The sciatic nerve was exposed in the middle region of the thigh, moving away the femoral biceps muscle. Close to the trifurcation of the sciatic nerve, 7 mm of distance from the trifurcation, 4 loose ligations were performed (chromed catgut 4-0) around it, distant from each other in approximately 1 mm. The bindings were performed along the nerve, up to 4-5 mm from the initial point. The incision was sutured in layers, using silk suture thread number 4-0.

EXAMPLE 11A

Evaluation of Hyperalgesia

For evaluation of hyperalgesia, rat paw pressure test was used (Analgesy-Meter Ugo Basile®, Italy), preformed in accordance with the method described by Randall & Sellito (1957). The test was applied before (BM-basal measurement) and on the $14^{th}$ day after the surgery, to characterize the development of neuropathic pain. On the $14^{th}$ day after surgery, the test was applied before (initial measurement —IM) and 1, 3, 24, 48, 72 and 96 hours after the administration of the synthetic peptide, in the doses of 0.0016; 0.008; 0.04; 0.2; 1 and 5 μg/kg, by oral route, or saline, as control (Table 11).

The results were analyzed by comparing the means of the basal and initial measurements or by comparing the means of the initial and final measurements or, when determined, through the comparison of the means obtained in the different experimental groups. The data represent the means±S.E.M of 5 animals per group.

TABLE 11

DURATION OF THE ANTINOCICEPTIVE EFFECT OF THE
SYNTHETIC PEPTIDE SEQ ID NO: 2 ON HYPERALGESIA INDUCED BY
CONSTRICTION OF THE SCIATIC NERVE.

| Treatments | BM | IM | FM 1 h | FM 3 h | FM 24 h | FM 48 h | FM 72 h | FM 96 h |
|---|---|---|---|---|---|---|---|---|
| Saline | 73 ± 1.44 | 33 ± 1.44* | 30 ± 0.00* | 30 ± 0.00* | 30 ± 0.00* | 34 ± 1.25* | 33 ± 1.44* | 33 ± 1.44* |
| P 0.0016 | 72 ± 1.22 | 33 ± 1.22* | 32 ± 1.22* | 32 ± 1.22* | 33 ± 1.22* | 30 ± 0.00* | 32 ± 1.22* | 32 ± 1.22* |
| P 0.008 | 74 ± 1.87 | 33 ± 1.22* | 34 ± 1.00* | 30 ± 1.58* | 30 ± 0.00* | 33 ± 1.22* | 31 ± 1.00* | 32 ± 1.22* |
| P 0.04 | 71 ± 1.00 | 33 ± 1.22* | 29 ± 1.00* | 30 ± 0.00* | 31 ± 1.00* | 33 ± 1.22* | 33 ± 0.00* | 33 ± 1.22* |
| P 0.2 | 73 ± 1.22 | 31 ± 1.00* | 51 ± 1.87*§# | 56 ± 1.87*§# | 52 ± 1.22*§# | 54 ± 1.00*§# | 53 ± 1.22*§# | 33 ± 1.22* |
| P 1 | 72 ± 1.22 | 31 ± 1.00* | 73 ± 1.22§# | 73 ± 1.22§# | 71 ± 1.00§# | 74 ± 1.00§# | 71 ± 1.00§# | 33 ± 1.22* |
| P 5 | 72 ± 0.79 | 32 ± 0.79* | 100 ± 4.42*§# | 98 ± 4.28*§# | 99 ± 3.51*§# | 93 ± 3.00*§# | 86 ± 2.45*§# | 33 ± 1.18* |

BM = basal measurement before surgery,
IM = initial measurement on the 14$^{th}$ day after surgery, before the administration of the peptide,
FM = final measurement on the 14$^{th}$ day after surgery, in different times after peptide or saline administration
g = weight in grams
Peptide doses in µg/kg.
Peptide or saline were administered on the 14$^{th}$ day, immediately after the determination of the 1M. The values of BM, IM and FM are represented in grams (g) ± S.E.M.
*p < 0.05 significantly different from means values of basal measurement
§p < 0.05 significantly different from means values on the 14$^{th}$ day
p < 0.05 significantly different from means values of control group (saline).

The obtained data demonstrated that the peptide was able to induce anti-hyperalgesic effect, in the neuropathic pain model, detected up to 3 days after one single administration.

The results obtained 1 hour after the treatment of the animals with the synthetic peptide, in the doses of 0.0016; 0.008; 0.04; 0.2 and 1 µg/kg, were used for the determination of the effective doses 50, 60 and 90%. The data were analyzed determining the percentage of decrease of the pain threshold (hyperalgesia), comparing the basal and initial measurements, followed by the determination of the percentage of reversal of hyperalgesia, comparing the treated (peptide) and control (saline) groups. These data were analyzed using CurveExpert 1.3 program. The results demonstrated that 50, 60 and 90% effective doses of the peptide, in this example, correspond to 0.205517; 0.283173 and 0.5747158 µg/kg, respectively.

EXAMPLE 11B

Determination of the Allodynia

Allodynia was evaluated for quantitative testing, in response to tactile stimulus applied to the paws of the rat, according to the method described by Chaplan el al. (1994), modified. In this test, the rats were placed, individually, in plastic cages, with meshed wire at the bottom, to allow access to the paws of these animals. Briefly, a logarithmic series of 10 calibrated Semmes-Weinstein monofilaments (von Frey hairs, Aesthesiometer Semmer-Weinstein, Stoelting Co., E.U.A) was applied to the right hind paw to determine the stimulus intensity threshold stiffness required to elicit a paw withdrawal response. Log stiffness of the hairs is determined by log 10 (mg×10) having the following values (the value in grams is between parenthesis): 3.61 (0.407 g); 3.84 (0.692 g); 4.08 (1.202 g); 4.17 (1.479 g); 4.31 (2.041 g); 4.56 (3.630 g); 4.74 (5.495 g); 4.93 (8.511 g); 5.07 (11.749 g) and 5.18 (15.136 g). It is important to point out that the filaments with weight greater than 15.136 g were not employed in the studies of allodynia.

The filaments were applied, one by one, perpendicularly, under the plantar area of both hind paws and maintained for a period of 8 seconds. The filament capable of eliciting the withdrawal of the paw, two consecutive times, was considered as the force in grams necessary to elicit the response (100% of response). In the absence of a response to the greater stimulus (15.135 g), this filament was considered as cut value.

The behavioral responses were used to calculate the 50% paw withdrawal threshold (absolute threshold), by fitting a gaussian integral psychometric function, using a maximum-likelihood fitting method. This fitting method allows parametric analyses.

The period of the application of the test and the treatments were the same as those used for determination of hyperalgesia (Table 12).

The results were analyzed by comparing the means of the basal and initial measurements or, when determined, by comparing the means obtained in the different experimental groups. The data represents the means±S.E.M. of 5 animals per group.

TABLE 12

DETERMINATION OF THE ANTINOCICEPTIVE EFFECT OF THE
SYNTHETIC PEPTIDE SEQ ID NO: 2 ON ALLODYNIA INDUCED BY
CONSTRICTION OF THE SCIATIC NERVE.

| Treatments | BM | IM | FM 1 h | FM 3 h | FM 24 h | FM 48 h | FM 72 h | FM 96 h |
|---|---|---|---|---|---|---|---|---|
| Saline | 5.04 ± 0.02* | 4.23 ± 0.01* | 4.22 ± 0.00* | 4.22 ± 0.00* | 4.22 ± 0.00* | 4.22 ± 0.00* | 4.22 ± 0.00* | 4.22 ± 0.00* |
| P 0.0016 | 5.02 ± 0.03 | 4.22 ± 0.00* | 4.22 ± 0.00* | 4.22 ± 0.00* | 4.22 ± 0.00* | 4.22 ± 0.00* | 4.22 ± 0.00* | 4.22 ± 0.00* |
| P 0.008 | 4.99 ± 0.02 | 4.22 ± 0.00* | 4.22 ± 0.00* | 4.22 ± 0.00* | 4.22 ± 0.00* | 4.22 ± 0.00* | 4.22 ± 0.00* | 4.22 ± 0.00* |
| P 0.04 | 4.97 ± 0.99 | 4.22 ± 0.00* | 4.22 ± 0.00* | 4.22 ± 0.00* | 4.22 ± 0.00* | 4.26 ± 0.04* | 4.22 ± 0.00* | 4.22 ± 0.00* |
| P 0.2 | 5.03 ± 0.02 | 4.22 ± 0.00* | 4.41 ± 0.00*§# | 4.41 ± 0.00*§# | 4.41 ± 0.00*§# | 4.41 ± 0.00*§# | 4.41 ± 0.00*§# | 4.22 ± 0.00* |

TABLE 12-continued

DETERMINATION OF THE ANTINOCICEPTIVE EFFECT OF THE
SYNTHETIC PEPTIDE SEQ ID NO: 2 ON ALLODYNIA INDUCED BY
CONSTRICTION OF THE SCIATIC NERVE.

| Treatments | BM | IM | FM 1 h | FM 3 h | FM 24 h | FM 48 h | FM 72 h | FM 96 h |
|---|---|---|---|---|---|---|---|---|
| P 1 | 5.06 ± 0.02 | 4.23 ± 0.01* | 4.62 ± 0.00*§# | 4.62 ± 0.00*§# | 4.62 ± 0.00*§# | 4.62 ± 0.00*§# | 4.62 ± 0.00*§# | 4.22 ± 0.00 |
| P 5 | 4.99 ± 0.03 | 4.23 ± 0.00* | 4.94 ± 0.05§# | 4.98 ± 0.04§# | 4.97 ± 0.03§# | 4.93 ± 0.04§# | 4.85 ± 0.02§# | 4.21 ± 0.01§# |

BM = basal measurement before surgery,
IM = initial measurement of the 14$^{th}$ day after surgery, before the administration of the peptide;
FM = final measurement of the 14$^{th}$ day after surgery, in different periods after peptide or saline administration;
data expressed as log 10 (mg × 10) ± S.E.M.
Peptide doses in μg/kg.
Peptide or saline were administered on the 14$^{th}$ day, immediately after the determination of the IM.
*p < 0.05 significantly different from means values of basal measurement
§p < 0.05 significantly different from means values on the 14$^{th}$ day
p < 0.05 significantly different from means values of control group (saline).

The data demonstrated that the peptide was able to induce anti-allodynic effect, in the neuropathic pain model, detected up to 3 days after one single administration.

EXAMPLE 11C

Determination of Spontaneous Pain

For the evaluation of spontaneous pain, the rats were observed on the 14th day after sciatic nerve constriction surgery, before and 1, 3, 24, 48, 72, 96, 120 and 144 hours after the administration of the peptide (5 μg/kg) or saline, by oral route (Tables 13 and 14). For the observation of the signs that characterize spontaneous pain, the animals were placed one by one, in a transparent plastic box. After the acclimatizing period of 30 minutes, the rats were observed during 10 minutes, determining the duration of the licking (in seconds) and lifting time. The licking and lifting activities, performed as part of the normal grooming behavior of animals, were not considered.

TABLE 13

ANTINOCICEPTIVE EFFECT OF THE SYNTHETIC PEPTIDE
CNF021.03 ON THE SPONTANEOUS PAIN INDUCED BY CONSTRICTION OF
THE SCIATIC NERVE - DURATION OF THE LICKING TIME (IN S) OF THE PAW

| Treatments | IM | FM 1 h | FM 3 h | FM 24 h | FM 48 h | FM 72 h | FM 96 h | FM 120 |
|---|---|---|---|---|---|---|---|---|
| Saline | 24 ± 0.6 | 21 ± 0.3 | 20 ± 0.8 | 21 ± 0.5 | 21 ± 0.5 | 22 ± 0.6 | 22 ± 0.5 | 22 ± 0.6 |
| Peptide | 22 ± 0.64 | 2 ± 0.21*# | 2 ± 0.21*# | 2 ± 0.39*# | 1.5 ± 0.22*# | 1.5 ± 0.22*# | 21 ± 0.26 | 21 ± 0.38 |

IM = initial measurement on the 14$^{th}$ day after surgery, before the administration of the peptide;
FM = final measurement on the 14$^{th}$ day after surgery, in different times after peptide or saline administration
Data expressed as paw licking time (in seconds). The data represent the means ± S.E.M. of 5 animals per group.
*p < 0.05 significantly different from means values of initial measurement
p < 0.05 significantly different from means values of control group (saline).

TABLE 14

ANTINOCICEPTIVE EFFECT OF THE SYNTHETIC PEPTIDE
CNF021.03 ON SPONTANEOUS PAIN INDUCED BY CONSTRICTION OF THE
SCIATIC NERVE-DURATION OF THE LIFTING TIME (IN S)

| Treatments | IM | FM 1 h | FM 3 h | FM 24 h | FM 48 h | FM 72 h | FM 96 h | FM 120 |
|---|---|---|---|---|---|---|---|---|
| Saline | 97 ± 0.37 | 97 ± 0.42 | 96 ± 0.58 | 96 ± 0.42 | 96 ± 0.48 | 95 ± 0.47 | 96 ± 0.40 | 96 ± 0.51 |
| Peptide | 97 ± 0.43 | 2 ± 0.21*# | 2 ± 0.26*# | 2 ± 0.22*# | 1.0 ± 0.16*# | 2 ± 0.26*# | 1.5 ± 0.16*# | 95 ± 0.50 |

IM = initial measurement on the 14$^{th}$ day after surgery, before the administration of the peptide;
FM = final measurement on he 14$^{th}$ day after surgery, in different times after peptide or saline administration
Data expressed as lifting time (in seconds). The data represent the means ± S.E.M. of 5 animals per group.
*p < 0.05 significantly different from means values of initial measurement
p < 0.05 significantly different from means values of control group (saline).

The results demonstrate that the peptide was able to interfering with both the licking and the lifting times (Tables 13 and 14), showing the inhibitory effect of this peptide on spontaneous pain in the neuropathic pain model.

EXAMPLE 12

Involvement of Opioid Receptors in the Antinociceptive Effect of the Synthetic Peptide SEQ ID NO: 2, in the Sciatic Nerve Constriction Model After demonstrating the antinociceptive effect of the peptide in hyperalgesia and allodynia induced by chronic constriction of the sciatic nerve, the involvement of opioid receptors in this effect was investigated. For this purpose, the animals were treated with CTOP, a specific μ receptor antagonist (20 μg/paw), nor-BNI, a specific κ receptor antagonist (50 μg/paw) or with ICI 174,864, a specific δ receptor antagonist (10 μg/paw). The antagonists were injected, by intraplantar route. The peptide was administered in the dose of 5 μg/kg, orally, immediately before the injection of the opioid antagonists.

The results were analyzed comparing the mean values of the basal and initial measurements, or of the initial and final measurements or, when determined, by comparing the mean values obtained in the different experimental groups (Tables 15 and 16).

TABLE 15

CHARACTERIZATION OF THE INVOLVEMENT OF OPIOID RECEPTORS IN THE ANTI-HYPERALGESIC EFFECT OF THE SYNTHETIC PEPTIDE SEQ ID NO: 2, IN NEUROPATHIC PAIN MODEL

| Treatments | BM | IM | FM 1 h | MF 3 h |
|---|---|---|---|---|
| Saline (p.o.) | 73 ± 1.66 | 37 ± 3.33* | 35 ± 0* | 30 ± 0* |
| Peptide (p.o.) | 72 ± 1.44 | 35 ± 2.04* | 114 ± 6.57*§# | 121 ± 5.91*§# |
| Peptide + ICI (i.pl.) | 72 ± 1.22 | 34 ± 1.87* | 35 ± 1.87* | 37 ± 2.55* |
| Peptide + norBNI (i.pl.) | 73 ± 1.22 | 35 ± 1.58* | 69 ± 1.87*§# | 75 ± 1.58*§# |
| Peptide + CTOP (i.pl.) | 72 ± 1.22 | 41 ± 1.88* | 105 ± 4.18*§# | 112 ± 5.83*§# |
| Saline + ICI (i.pl.) | 71 ± 1.00 | 31 ± 1.00* | 32 ± 1.22* | 31 ± 1.00* |
| Saline + norBNI (i.pl.) | 72 ± 1.22 | 32 ± 1.22* | 32 ± 1.22* | 31 ± 1.00* |
| Saline + CTOP (i.pl.) | 72 ± 1.22 | 28 ± 1.22* | 30 ± 1.58* | 30 ± 1.58* |

BM = basal measurement before surgery,

IM = initial measurement on the $14^{th}$ day after surgery, before the administration of the peptide, FM = final measurement on the $14^{th}$ day after surgeryl, in different times after the administration of the peptide or saline (control), data are presented as the mean of grams (g) ± S.E.M p < 0.05 Significantly different from mean values of basal measurement §p < 0.05 Significantly different from mean values of initial measurement on the $14^{th}$ day p < 0.05 Significantly different from mean values of control group (saline).

The data demonstrated that the delta opioid receptor antagonist blocked the anti-hyperalgesic effect of the peptide in the model of chronic constriction of the sciatic nerve. The kappa opioid receptor antagonist partially inhibited this effect. The mu opioid receptor antagonist did not alter the peptide effect.

TABLE 16

CHARACTERIZATION OF THE INVOLVEMENT OF OPIOID RECEPTORS IN THE ANTI-ALLODYNIC EFFECT OF SYNTHETIC PEPTIDE SEQ ID NO: 2, IN NEUROPATHIC PAIN MODEL

| Treatments | BM | IM | FM 1 h | FM 3 h |
|---|---|---|---|---|
| Saline (p.o.) | 5.03 ± 0.03 | 4.28 ± 0.06* | 4.22 ± 0* | 4.22 ± 0* |
| Peptide (p.o.) | 5.00 ± 0.03 | 4.27 ± 0.04* | 5.08 ± 0.01§# | 5.09 ± 0§# |
| Peptide + ICI (i.pl.) | 4.96 ± 0.04 | 4.29 ± 0.04* | 4.22 ± 0* | 4.22 ± 0* |
| Peptide + norBNI (i.pl.) | 5.03 ± 0.02 | 4.25 ± 0.03* | 4.62 ± 0*§# | 4.62 ± 0*§# |
| Peptide + CTOP (i.pl.) | 4.99 ± 0.02 | 4.29 ± 0.04* | 5.00 ± 0.05§# | 4.99 ± 0.02§# |
| Saline + ICI (i.pl.) | 5.08 ± 0.01 | 4.22 ± 0* | 4.22 ± 0* | 4.22 ± 0* |
| Saline + norBNI (i.pl.) | 5.08 ± 0 | 4.22 ± 0* | 4.22 ± 0* | 4.22 ± 0* |
| Saline + CTOP (i.pl.) | 5.08 ± 0 | 4.22 ± 0* | 4.22 ± 0* | 4.22 ± 0* |

BM = basal measurement before surgery,

IM = initial measurement on the $14^{th}$ day after surgery, before the administration of the peptide, FM = final measurement on the $14^{th}$ day after surgeryl, in different times after the administration of the peptide or saline (control). The peptide or saline were administered on the $14^{th}$ day immediately after the determination of the IM. The values of the IMs and FMs are represented as the mean of log 10 (mg × 10) ± S.E.M.

p < 0.05 Significantly different from mean values of basal measurement

§p < 0.05 Significantly different from mean values of initial measurement on the $14^{th}$ day p < 0.05 Significantly different from mean values of control group (saline).

The data demonstrated that delta opioid receptor antagonist blocked the anti-allodynic effect of the peptide in the model of chronic constriction of the sciatic nerve. The kappa opioide receptor antagonist partially inhibited this effect, while mu receptors antagonist-did not alter the effect of the peptide.

EXAMPLE 13

Analgesic Activity of the Synthetic Peptide SEQ ID NO: 2 in Cancer Pain, a Persistent Pain Model—Studies with the Walker 256 Tumor The Walker 256 tumor cells were kindly provided by Prof. Dr. Rui Curi, of the Physiology and Biophysics Department of the Biomedical Science Institute of the University of São Paulo. The tumor-bearing animal was sacrificed and the tumoral tissue was removed, placed on a Petri dish containing 0.9% saline. Then, the tumor was cut in smaller parts, and transferred into a beaker containing saline. The material was triturated with a fine-cut, until the tumor is totally fragmented. Then, this material was filtered in gauze and the liquid collected in a beaker. All procedures were performed on ice. The material of the beaker was transferred to 50 ml plastic tubes and centrifuged at 4° C., for 10 minutes, at 1200 rpm. After centrifugation, the supernatant was rejected and the precipitate resuspended in saline 0.9%. For cell counts, the suspension of cells was diluted (1:100) in saline. An aliquot (200 µl) was removed and placed in a test tube containing 200 µl of 1% Trypan blue. The cell number was determined in optical microscope using Neubauer's chamber. The cellular viability was determined considering viable the light-refracting cells.

After determining the number of cells, 1 ml of the suspension, containing $1 \times 10^7$ cells, was injected by intraperitoneal route, on the right side of the rats to obtain liquid tumor (ascites).

Five days after injection, the rats with ascites were sacrificed and the ascetic fluid collected from the peritoneal cavity and placed in a test tube containing EDTA. The liquid was diluted 100 times with phosphate-buffered saline (PBS), pH 7.4. The cell count was done after dilution with Trypan blue, as described above. Tumor cell count was ascertained to $1 \times 106$ cells in 100 µl, by dilution with PBS. This number of cells was determined in preliminary tests for induction of cancer pain in rats. In this final cell number adjustment, the volume of antibiotic (Benzetacil®) added to the suspension (150,000 units of antibiotic/10 ml of suspension), was taken into consideration. The antibiotic was used in order to avoid microbial contamination. The cells were injected by intraplantar route into one of the rat hind paws. Control animals were injected with PBS into the contralateral paw, in the same experimental conditions.

For evaluation of the antinociceptive effect of the synthetic peptide in this model, the animals were treated with the peptide, in the dose of 6 µg/kg, or saline (control), orally, 5 days after Walker tumor cell injection. Hyperalgesia, allodynia and spontaneous pain were determined before (BM-basal measurement) and 5 days after tumor cell injection, before (IM-initial measurement) and 2 hours after (FM-Final measurement) peptide administration.

The results were analyzed comparing the mean values of the basal and initial measurements, or of the initial and final measurements or, when determined, by comparing the mean values obtained in the different experimental groups (Tables 17, 18, 19).

TABLE 17

ANTINOCICEPTIVE EFFECT OF THE SYNTHETIC PEPTIDE CNF021.03 ON HYPERALGESIA INDUCED BY THE WALKER 256 TUMOR

| Treatments | BM | IM | FM |
| --- | --- | --- | --- |
| Saline (p.o.) | 69 ± 1.42 | 29 ± 2.97* | 29 ± 2.29* |
| Petide (6 µg/kg, p.o.) | 69 ± 1.30 | 27 ± 1.01* | 76 ± 2.29§# |

BM = basal measurement before the injection of the tumor,
IM = measurement of the $5^{th}$ day after the implantation of the tumor, before the administration of the peptide,
FM = measurement of the $5^{th}$ day after the implantation of the tumor and 2 hours after the administration of the peptide, data are presented as the mean of grams (g) ± S.E.M
*$p < 0.05$ Significantly different from mean values of basal measurement
§$p < 0.05$ Significantly different from mean values of initial measurement on the $5^{th}$ day
$p < 0.05$ Significantly different from mean values of control group (saline).

TABLE 18

ANTINOCICEPTIVE EFFECT OF THE SYNTHETIC PEPTIDE CNF021.03 ON ALLODYNIA INDUCED BY THE WALKER 256 TUMOR.

| Treatments | BM | IM | FM |
| --- | --- | --- | --- |
| Saline (p.o.) | 5.01 ± 0.04 | 4.41 ± 0.00* | 4.41 ± 0.00* |
| Peptide (6 µg/kg, p.o.) | 4.97 ± 0.00 | 4.41 ± 0.00* | 4.97 ± 0.00§# |

BM = basal measurement before the injection of the tumor,
IM = measurement of the $5^{th}$ day after the implantation of the tumor, before the administration of the peptide,
FM = measurement on the $5^{th}$ day after the implantation of the tumor and 2 hours after the administration of the peptide, data are presented as the mean value of log 10 (mg × 10) ± S.E.M.
*$p < 0.05$ Significantly different from mean values of basal measurement
§$p < 0.05$ Significantly different from mean values of initial measurement on the $5^{th}$ day
$p < 0.05$ Significantly different from mean values of control group (saline).

TABLE 19

ANTINOCICEPTIVE EFFECT OF THE SYNTHETIC PEPTIDE CNF021.03 ON SPONTANEOUS PAIN INDUCED BY THE WALKER 256 TUMOR

| | Lifting | | | Licking | | |
| --- | --- | --- | --- | --- | --- | --- |
| Treatments | BM | IM | FM | BM | IM | FM |
| Saline (p.o.) | 0 ± 0.00 | 107 ± 10.52* | 117 ± 15.16* | 0 ± 0.00 | 17 ± 4.91* | 16 ± 4.66* |
| Peptide (6 µg/kg, p.o.) | 0 ± 0.00 | 204 ± 30.74* | 25 ± 7.72*§# | 0 ± 0.00 | 15 ± 1.46* | 1.6 ± 0.81*§# |

BM = basal measurement before the injection of the tumor,
IM = measurement on the $5^{th}$ day after the implantation of the tumor, before the administration of the peptide;
FM = measurement on the $5^{th}$ day after the implantation of the tumor and 2 hours after the administration of the peptide, data are presented as the mean value of duration (in seconds) of lifting or licking of the hind paws ± S.E.M.
*$p < 0.05$ Significantly different from mean values of basal measurement
§$p < 0.05$ Significantly different from mean values of initial measurement on the $5^{th}$ day
$p < 0.05$ Significantly different from mean values of control group (saline).

The results demonstrated that the peptide blocks hyperalgesia (Table 17), allodynia (Table 18) and spontaneous pain (Table 19) induced by the Walker tumor. These data showed that the peptide is able to inhibit cancer pain.

EXAMPLE 14

Evaluation of the Involvement of Opioid Receptors in the Antinociceptive Effect of the Synthetic Peptide SEQ ID NO: 2 in the Model of Cancer Pain Induced by Walker 256 Tumor After demonstrating the antinociceptive effect of the peptide on hyperalgesia and allodynia induced by the Walker 256 tumor, the involvement of opioid receptors in this effect was investigated. For this purpose, the animals were treated with CTOP, a specific μ receptor antagonist (20 μg/paw), nor-BNI, a specific κ receptor antagonist (50 μg/paw) or with ICI 174,864, a specific δ receptor antagonist (10 μg/paw). The antagonists were injected by intraplantar route. The peptide was administered in the dose of 6 μg/kg, orally, immediately before the injection of the opioid antagonists. The results were analyzed comparing the mean values of the basal and initial measurements, or of the initial and final measurements or, when determined, by comparing the mean values obtained in the different experimental groups (Table 20).

TABLE 20

CHARACTERIZATION OF THE INVOLVEMENT OF OPOID RECEPTORS IN THE ANTI-HYPERALGESIC EFFECT OF THE SYNTHETIC PEPTIDE SEQ ID NO: 2 IN THE CANCER MODEL INDUCED BY THE WALKER 256 TUMOR

| Treatments | BM | IM | FM |
|---|---|---|---|
| Saline (p.o.) | 68 ± 1.66 | 40 ± 0.00* | 38 ± 1.66* |
| Peptide (p.o.) | 71 ± 1.25 | 36 ± 2.39* | 75 ± 2.88§# |
| Peptide + ICI (i.pl.) | 67 ± 1.22 | 33 ± 3.39* | 52 ± 1.22*§# |
| Peptide + norBNI (i.pl.) | 69 ± 1.53 | 32 ± 2.14* | 32 ± 1.05* |
| Peptide + CTOP (i.pl.) | 70 ± 1.29 | 37 ± 2.81* | 72 ± 2.81§# |
| Saline + ICI (i.pl.) | 68 ± 3.33 | 30 ± 2.88* | 30 ± 2.88* |
| Saline + norBNI (i.pl.) | 70 ± 2.88 | 33 ± 3.33* | 32 ± 1.66* |
| Saline + CTOP (i.pl.) | 68 ± 1.66 | 35 ± 2.88* | 32 ± 1.66* |

BM = basal measurement before the injection of the tumor,
IM = measurement on the 5th day after the implantation of the tumor, before the administration of the peptide,
FM = measurement on the 5th day after the implantation of the tumor and 2 hours after the administration of the peptide, data are presented as the mean of grams (g) ± S.E.M
*$p < 0.05$ Significantly different from mean values of basal measurement
§$p < 0.05$ Significantly different from mean values of initial measurement on the 5th day
$p < 0.05$ Significantly different from mean values of control group (saline).

The data demonstrated that the kappa opioid receptor antagonist blocked the anti-hyperalgesic effect of the peptide. The delta opioid receptor antagonist partially inhibited this effect, while the mu opioid receptor antagonist did not alter the effect of the peptide.

TABLE 21

CHARACTERIZATION OF THE INVOLVEMENT OF OPIOID RECEPTORS IN THE ANTI-ALLODYNIC EFFECT OF THE SYNTHETIC PEPTIDE SEQ ID NO: 2, IN THE CANCER MODEL INDUCED BY THE WALKER 256 TUMOR

| Treatments | BM | IM | FM |
|---|---|---|---|
| Saline (p.o.) | 5.01 ± 0.04 | 4.41 ± 0.00* | 4.59 ± 0.18* |
| Peptide (p.o.) | 4.97 ± 0.00 | 4.41 ± 0.00* | 4.97 ± 0.00§# |
| Peptide + ICI (i.pl.) | 4.99 ± 0.02 | 4.41 ± 0.00* | 4.56 ± 0.03*§# |
| Peptide + norBNI (i.pl.) | 4.97 ± 0.00 | 4.41 ± 0.00* | 4.41 ± 0.00* |
| Peptide + CTOP (i.pl.) | 5.03 ± 0.02 | 4.41 ± 0.00* | 4.98 ± 0.03*# |
| Saline + ICI (i.pl.) | 4.97 ± 0.00 | 4.41 ± 0.00* | 4.41 ± 0.00* |
| Saline + norBNI (i.pl.) | 4.97 ± 0.00 | 4.41 ± 0.00* | 4.41 ± 0.00* |
| Saline + CTOP (i.pl.) | 4.97 ± 0.00 | 4.41 ± 0.00* | 4.41 ± 0.00* |

BM = basal measurement before the injection of the tumor,
IM = measurement on the 5th day after the implantation of the tumor, before the administration of the peptide,
FM = measurement on the 5th day after the implantation of the tumor and 2 hours after the administration of the peptide, data are presented as the mean value of log 10 (mg × 10) ± S.E.M.
*$p < 0.05$ Significantly different from mean values of basal measurement
§$p < 0.05$ Significantly different from mean values of initial measurement on the 5th day
$p < 0.05$ Significantly different from mean values of control group (saline).

The data demonstrated that the kappa opioid receptor antagonist blocked the anti-allodynic effect of the peptide. The delta opioid receptor antagonist partially inhibited this effect, while the mu opioid receptor antagonist did not alter the effect of the peptide.

EXAMPLE 15

Evaluation of the Antinociceptive Effect of the Synthetic Peptide SEQ ID NO: 2 in the Hot Plate Test This test is used for evaluation of drugs that interfere with nociception in the Central Nervous System, as for example, morphine and derived products, since the thermal stimulus activates directly the nociceptor, avoiding tissue lesion and consequent inflammation. The data obtained in this test indicate that the antinociceptive effect of a compound is mainly due to a supraspinally integrated response.

This test was performed in accordance to the method described by Jacob, J. J. C. and Ramabadran, K. (Br. J. Pharmacol., 64:91-8, 1978). For this test, mice were placed on a metal surface kept at 50° C.±1. Results are expressed as the latency time (in seconds—s) to observe the licking of both anterior feet (reaction time). This test was applied before (initial measurement—IM) and 2 hours after the treatment of the animals (final measurement—FM) with saline (control) or with the synthetic peptide (1 and 3 μg/kg in 200 μl), orally. Each animal was considered as their own control. The results were analyzed comparing the mean values of the IM and FM or, when determined, by comparing the mean values obtained in the different experimental groups (Table 22).

TABLE 22

ANTINOCICEPTIVE EFFECT OF THE SYNTHETIC PEPTIDE SEQ ID NO: 2, EVALUATED IN THE HOT PLATE TEST

| Treatment | IM (s) ± S.E.M. | FM (s) ± S.E.M. |
|---|---|---|
| Saline (p.o.) | 19 ± 0.54 | 19 ± 0.45 |
| Peptide 1 μg/kg (p.o.) | 18 ± 0.64 | 25 ± 0.68* |
| Peptide 3 μg/kg (p.o.) | 22 ± 1.01 | 27 ± 1.06* |

IM = initial measurement;
FM = final measurement; data are presented as the mean of grams (g) ± S.E.M
*$p < 0.05$ Significantly different from mean values of initial measurement.
The results demonstrate that the synthetic peptide induces antinociception also by an action in the Central Nervous System.

EXAMPLE 16

Antinociceptivec Activity of the Modified Synthetic Peptide SEQ ID NO: 3

For induction of hyperalgesia, prostaglandin $E_2$, in the dose of 100 ng/paw was administered by intraplantar (i.pl.) route. Hyperalgesia was evaluated before (initial measurement—IM) and 3 hours after (final measurement—FM) $PGE_2$ injection.

For hyperalgesia evaluation, the rat paw pressure test was used. The pain threshold, represented by the force (in grams) that makes the animal reacts withdrawing the paw, was determined before (initial measurement) and 3 hours after (final measurement) the intraplantar injection of prostaglandin $E_2$ (100 ng/leg).

The modified synthetic peptide SEQ ID NO: 3 was diluted in a volume of 11 ml of saline. Each animal received 2 ml of this solution, administered orally (p.o.), immediately before hyperalgesia induction. Animals injected with saline, orally, were used as control.

| Treatments | IM (grams) ± S.E.M. | FM (grams) ± S.E.M. |
|---|---|---|
| Saline (p.o.) + $PGE_2$ (i.pl.) | 76 ± 1.05 | 59 ± 1.54* |
| Peptide (p.o.) + $PGE_2$ (i.pl.) | 76 ± 1.00 | 110 ± 2.74*# |

Data are presented as the mean of grams (g) ± S.E.M
*$p < 0.05$ Significantly different from mean values of initial measurement.
$p < 0.05$ Significantly different from mean values of control group (saline).

The results demonstrate the antinociceptive effect of the modified synthetic peptide SEQ ID NO: 3 in hyperalgesia induced by $PGE_2$.

SEQUENCE LISTING

```
<160> NUMBER OF SEQ ID NOS: 8

<210> SEQ ID NO 1
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = pyroglutamate
<220> FEATURE:
<221> NAME/KEY: VARIANT
<222> LOCATION: 2
<223> OTHER INFORMATION: Xaa = Phe or Trp or Tyr or Leu or Thr
<220> FEATURE:
<221> NAME/KEY: VARIANT
<222> LOCATION: 4
<223> OTHER INFORMATION: Xaa = Pro or Arg
<220> FEATURE:
<221> NAME/KEY: VARIANT
<222> LOCATION: 5
<223> OTHER INFORMATION: Xaa = Glx or Asx or Gly
<220> FEATURE:
<221> NAME/KEY: VARIANT
<222> LOCATION: 6
<223> OTHER INFORMATION: Xaa = Asn or Gln or Leu
<220> FEATURE:
<221> NAME/KEY: VARIANT
<222> LOCATION: 10
<223> OTHER INFORMATION: Xaa = Glx or Asx
<220> FEATURE:
<221> NAME/KEY: VARIANT
<222> LOCATION: 12
<223> OTHER INFORMATION: Xaa = Glx or Lys

<400> SEQUENCE: 1

Xaa Xaa Ser Xaa Xaa Xaa Cys Glx Gly Xaa Ser Xaa Pro Cys
 1               5                  10

<210> SEQ ID NO 2
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = pyroglutamate
```

```
<400> SEQUENCE: 2

Xaa Phe Ser Pro Glu Asn Cys Gln Gly Glu Ser Gln Pro Cys
 1               5                  10

<210> SEQ ID NO 3
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = pyroglutamate

<400> SEQUENCE: 3

Xaa Phe Ser Pro Glu Asn Cys Gln Gly Glu Ser Lys Pro Cys
 1               5                  10

<210> SEQ ID NO 4
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = pyroglutamate
<220> FEATURE:
<221> NAME/KEY: VARIANT
<222> LOCATION: 2
<223> OTHER INFORMATION: Xaa = Phe or Trp or Tyr or Leu or Thr
<220> FEATURE:
<221> NAME/KEY: VARIANT
<222> LOCATION: 4
<223> OTHER INFORMATION: Xaa = Pro or Arg
<220> FEATURE:
<221> NAME/KEY: VARIANT
<222> LOCATION: 5
<223> OTHER INFORMATION: Xaa = Glx or Asx or Gly
<220> FEATURE:
<221> NAME/KEY: VARIANT
<222> LOCATION: 6
<223> OTHER INFORMATION: Xaa = Asn or Gln or Leu
<220> FEATURE:
<221> NAME/KEY: VARIANT
<222> LOCATION: 10
<223> OTHER INFORMATION: Xaa = Glx or Asx
<220> FEATURE:
<221> NAME/KEY: VARIANT
<222> LOCATION: 12
<223> OTHER INFORMATION: Xaa = Glx or Lys
<220> FEATURE:
<221> NAME/KEY: MOD_RES
<222> LOCATION: 7, 14
<223> OTHER INFORMATION: Contain an intramolecular disulfide bridge
      betwen cysteine residues

<400> SEQUENCE: 4

Xaa Xaa Ser Xaa Xaa Xaa Cys Glx Gly Xaa Ser Xaa Pro Cys
 1               5                  10

<210> SEQ ID NO 5
<211> LENGTH: 8
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 4
<223> OTHER INFORMATION: Xaa = Glx or Asx
```

```
<220> FEATURE:
<221> NAME/KEY: VARIANT
<222> LOCATION: 6
<223> OTHER INFORMATION: Xaa = Glx or Lys

<400> SEQUENCE: 5

Cys Glx Gly Xaa Ser Xaa Pro Cys
 1               5

<210> SEQ ID NO 6
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa =  pyroglutamate

<400> SEQUENCE: 6

Xaa Phe Ser Pro Glu Asn Cys Lys Gly Glu Ser Gln Pro Cys
 1               5                  10

<210> SEQ ID NO 7
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = pyroglutamate

<400> SEQUENCE: 7

Xaa Phe Ser Pro Glu Asn Cys Lys Gly Glu Ser Lys Pro Cys
 1               5                  10

<210> SEQ ID NO 8
<211> LENGTH: 14
<212> TYPE: PRT
<213> ORGANISM: Artificial Sequence
<220> FEATURE:
<223> OTHER INFORMATION: Synthetically generated peptide, C-terminal
      portion of the crotapotin, non-toxic acidic subunit from
      the crotoxin of the snake venom of the Crotalus durissus
      terrificus species
<220> FEATURE:
<221> NAME/KEY: VARIANT
<222> LOCATION: 1
<223> OTHER INFORMATION: Xaa = pyroglutamate

<400> SEQUENCE: 8

Xaa Phe Ser Pro Glu Asn Cys Gln Gly Glu Ser Gln Pro Cys
 1               5                  10
```

The invention claimed is:

1. A purified peptide comprising the amino acid sequence: Xaa-Phe-Ser-Pro-Glu-Asn-Cys-Gln-Gly-Glu-Ser-Lys-Pro-Cys (SEQ ID NO:3), wherein Xaa is pyroglutamate; and wherein the cysteine residues in positions 7 and 14 are linked by an intramolecular disulfide bridge; or a salt thereof, wherein the peptide is capable of causing analgesia in a subject.

2. A pharmaceutical composition comprising the peptide of claim 1.

3. A process for producing the peptide of claim 1, wherein the process comprises peptide synthesis in solid phase.

4. A method of treating or diagnosing pain in a subject in need thereof, the method comprising administering to the subject an effective amount of the pharmaceutical composition of claim 2.

* * * * *